(12) United States Patent
Szebeni et al.

(10) Patent No.: US 7,419,683 B2
(45) Date of Patent: Sep. 2, 2008

(54) METHOD OF INHIBITING SIDE EFFECTS OF PHARMACEUTICAL COMPOSITIONS CONTAINING AMPHIPHILIC VEHICLES OR DRUG CARRIER MOLECULES

(75) Inventors: Janos Szebeni, Bethesda, MD (US); Carl R. Alving, Bethesda, MD (US)

(73) Assignee: United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/183,375

(22) Filed: Oct. 30, 1998

(65) Prior Publication Data
US 2002/0136759 A1 Sep. 26, 2002

(51) Int. Cl.
*A61K 38/00* (2006.01)
*A61K 31/00* (2006.01)
*A61K 9/127* (2006.01)

(52) U.S. Cl. .............................. 424/450; 514/1; 514/21
(58) Field of Classification Search ................. 424/450, 424/1.21, 9.321, 9.51, 94.3; 514/936–943, 514/1, 21
See application file for complete search history.

(56) References Cited

U.S. PATENT DOCUMENTS

| | | | | |
|---|---|---|---|---|
| 5,462,726 A | * | 10/1995 | Lodge | 514/558 |
| 5,478,860 A | * | 12/1995 | Wheeler et al. | 514/449 |
| 5,744,156 A | * | 4/1998 | De Lacharriere | 424/445 |
| 5,851,528 A | * | 12/1998 | Ko | 424/185.1 |
| 5,877,396 A | * | 3/1999 | Ravetch et al. | 800/3 |
| 6,495,735 B1 | * | 12/2002 | White et al. | 800/17 |

FOREIGN PATENT DOCUMENTS

| | | |
|---|---|---|
| EP | 0 584 001 A1 | 2/1994 |
| WO | WO 97/26862 | 7/1997 |

OTHER PUBLICATIONS

Decorti et al., 1996 "Effect of Paclitaxel and Cremophor EL on Mast Cell Histamine Secretion and Their Interaction with Adriamycin" Anticancer Research 16: 317-320.
Eisenhauer et al., 1994 "European-Canadian Randomized Trial of Paclitaxel in Relapsed Ovarian Cancer: High-Dose Versus Low-Dose and Long Versus Short Infusion" Journal of Clinical Oncology, 12(12): 2654-2666.
Essayan et al., 1996 "Successful Parenteral Desensitization to Paclitaxel" Journal of Allergy Clinical Immunology, 97(1): 42-46.

(Continued)

*Primary Examiner*—Gollamudi S Kishore
(74) *Attorney, Agent, or Firm*—Elizabeth Arwine; Charles H. Harris

(57) ABSTRACT

A method is provided for inhibiting or preventing toxicity and other unwanted effects (a) caused by solvents for pharmaceuticals which solvents or emulsifier which contain amphiphilic molecules such as polyethoxylated oils or a derivative thereof, or (b) caused by a drug in a vehicle containing amphiphilic molecules such as phopholipids or derivative thereof, emptying a complement inhibitor. Drug compositions containing amphiphilic molecules, or derivatives thereof and a complement inhibitor, and pharmaceutical compositions including a drug, solvent or carrier containing amphiphilic molecules or derivatives thereof, and a complement inhibitor are also provided.

9 Claims, 14 Drawing Sheets

OTHER PUBLICATIONS

Hammerschmidt et al., 1980 "Association of Complement Activation and Elevated Plasma-C5a With Adult Respiratory Distress Syndrome" The Lancet, May 3, 1980: 947-949.

Marceau et al., 1987 "Effects of the Anaphylatoxins on Circulation" Immunopharmacology, 14: 67-84.

Michaud, 1997 "Methods for Preventing Reactions Secondary to Cremophor EL" Annals of Pharmacotherapy, 31(11): 1402-1404.

O'Brien et al., 1992 "Allergic Reactions to Cytotoxic Drugs—an Update" Annals of Oncology, 3: 605-610.

Szebeni, 1998 "The Interaction of Liposomes with the Complement System" Critical Reviews in Therapeutic Drug Carrier Systems, 15(1): 57-88.

Szebeni et al, 1998 "Complement Activation by Cremophor EL as a Possible Contributor to Hypersensitivity to Paclitaxel: an In Vitro Study" Journal of the National Cancer Institute, 90(4): 300-306.

Szebeni et al., 1997 "Complement Activation In Vitro by the Red Cell Substitute, Liposome-encapsulated Hemoglobin: Mechanism of Activation and Inhibition by Soluble Complement Receptor Type 1" Transfusion, 37(2): 150-159.

Szebeni et al., 1997) "Complement Activation and Thromboxane Secretion by Liposome-Encapsulated Hemoglobin in Rats In Vitro: Inhibition by Soluble Complement Receptor Type 1" Art., Cells, Blood Subs., and Immob. Biotech., 25(4): 347-355.

Terwogt et al, 1997 "Alternative Formulations of Paclitaxel" Cancer Treatment Reviews 23(2): 87-95.

Wassef et al., 1989 "Anaphylactoid Reactions Mediated by Autoantibodies to Cholesterol in Miniature Pigs" The Journal of Immunology 143(8): 2990-2995.

Weiss et al., 1990 "Hypersensitivity Reactions From Taxol" Journal of Clinical Oncology, 8(7): 1263-1268.

\* cited by examiner

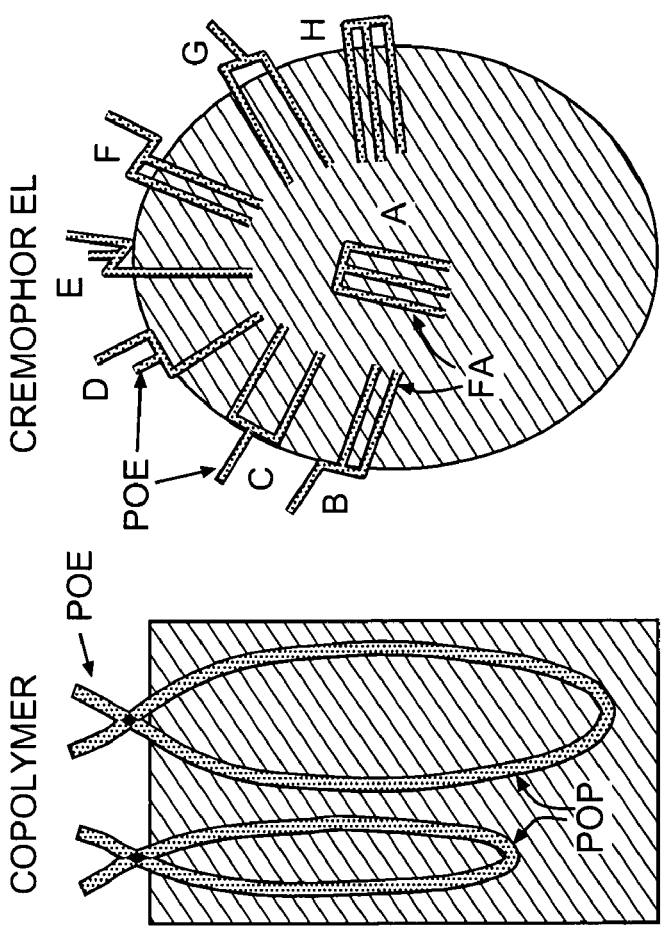
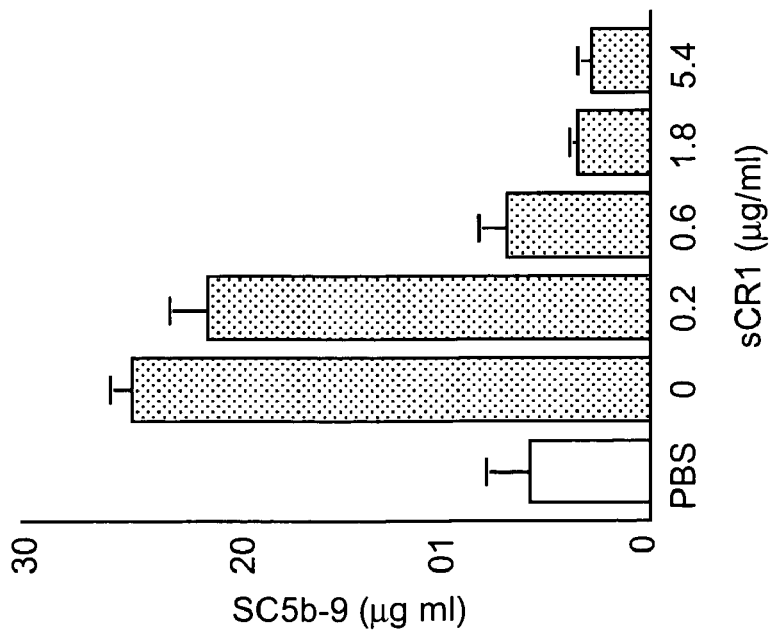
FIG. 4
FIG. 5A
FIG. 5B

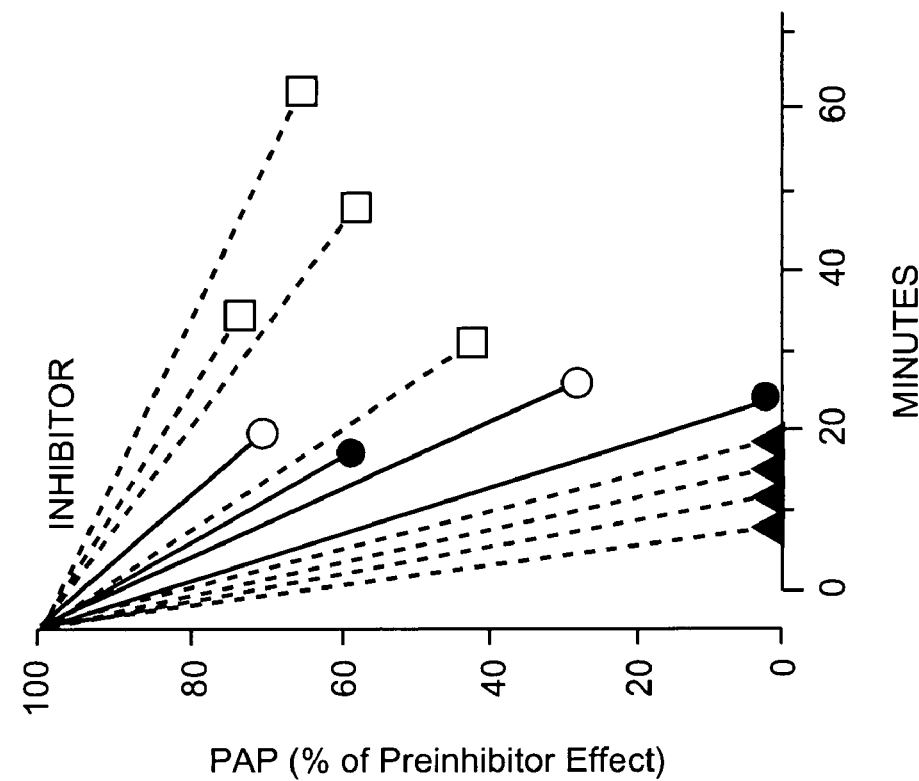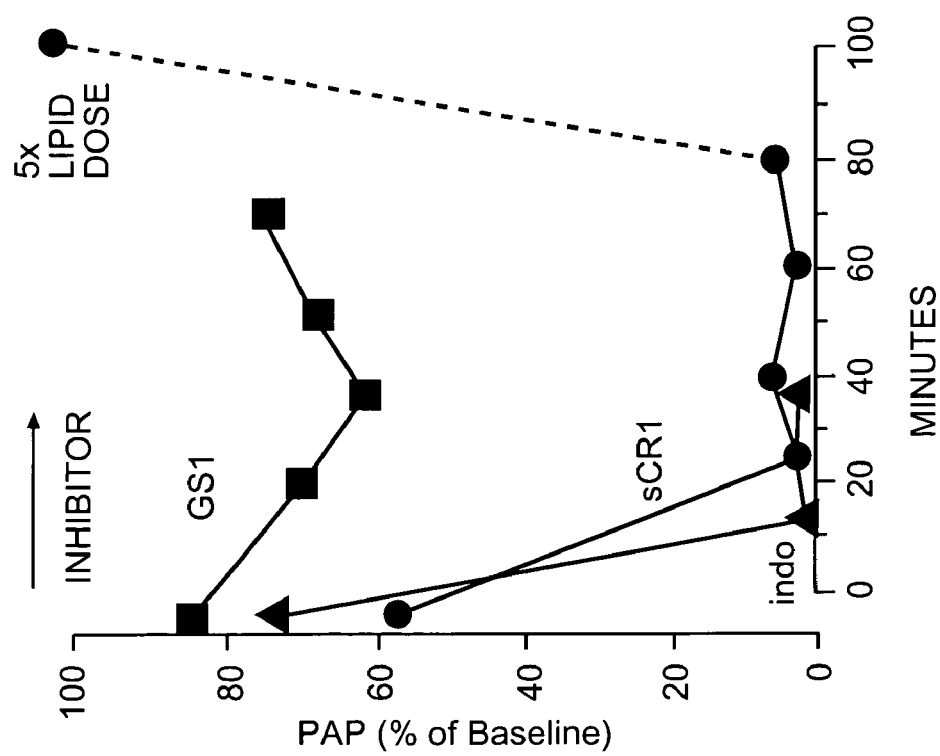

METHOD OF INHIBITING SIDE EFFECTS OF PHARMACEUTICAL COMPOSITIONS CONTAINING AMPHIPHILIC VEHICLES OR DRUG CARRIER MOLECULES

INTRODUCTION

The present invention relates to a method for inhibiting or preventing toxicity and other unwanted side effects caused by pharmaceutical compositions containing amphiphilic molecules as vehicles or carriers of the active agents, such as polyethoxylated oil-containing emulsifiers or liposomes, said method employing a complement activation inhibitor.

Amphiphilic molecules have both hydrophilic and hydrophobic parts, causing self-assembly in different multimolecular structures, such as micelles or planar sheets, called membranes. Detergents or emulsifiers containing amphiphilic molecules include, but are not limited to, polyethoxylated oils and derivatives thereof, and carriers such as liposomes. Polyethoxylated oils are oils, such as castor (ricinus) oil (i.e. oil comprised of a mixture of triglicerides with 90 ricinoleic acid-ester content), reacted with ethylene oxide at heat and pressure. Liposomes are bilayer membrane vesicles tightly enclosing an internal water space that may or may not contain drugs or other active agents.

The present invention also relates to complement inhibitors, which are molecules that inhibit the activation of the complement (C) system, a part of the human immune system. This activation involves a chain of enzymatic interactions between C proteins in the plasma that underlie the antimicrobial defense role of this system.

The present invention also relates pharmaceutical compositions including a drug, solvents or drug carriers containing amphiphilic molecules or a derivative thereof and a complement activation inhibitor.

BACKGROUND OF THE INVENTION

Polyethoxylated castor oil, providing different grade "Cremophors", have been employed as effective solvents or carriers for pharmaceuticals. For example, Cremophor EL is known for its use with an extensive array of pharmaceuticals including Miconazole (Handbook on Injectable Drugs), echinomycin (Handbook on Injectable Drugs), teniposide (Rowinsky et al. 1992, *Seminars in Oncology*, 19, 646), diazepam (Lau et al. 1989, *Int. J. Pharm.* 54, 171), althesin (Dye et al., 1980, Br. Med. J. 230, 1353) and taxol (Rowinsky et al., 1992, supra).

With its unique mechanism of action as a stabilizer of tubulin polymerization, paclitaxel (Taxol®) has become an important agent in current cancer chemotherapy. One problem associated with its clinical use has been the frequent presence of acute hypersensitivity reactions, characterized by dyspnea, flushing, rash, chest pain, tachycardia, hypotension, angioedema and generalized urticaria (Wiernic, P H et al., 1987, *J Clin Oncol.*, 5, 1232; Wiernic, P H et al., 1987, *Cancer Res.*, 47, 2486; Rowinsky, E K et al., 1992, *Semin. Oncol.*, 19, 646; Bristol-Myers Squibb Oncology Products Division, Princeton, N.J. Paxitaxel (Taxol) package insert, 1993; Rowinsky, E K, 1993, *Monogr. Natl. Cancer Inst.* 15, 25; Rowinsky, E K et al., 1993, *Semin. Oncol.*, 20, 1; Rowinsky, E K and Donehower, R C., 1993, *Semin. Oncol.* 20, 16; Sharma, A et al., 1993, *Cancer Res.* 53, 5877; Rowinsky, E K et al., 1994, *Ann. Oncol.*, 5, S7; Guchelaar, H J et al., 1994, *Clin. Oncol.* 6, 40; Essayan, D M et al. 1996, *J. Allergy Clin. Immunol.* 97, 42). All documents cited herein supra and infra are hereby incorporated in their entirety by reference thereto.

As a consequence of the death of a patient after being treated with paclitaxel during one of the initial clinical trials, it has become standard practice to administer this drug to patients in a 24-hour infusion after premedicating them with high-dose corticosteroids, e.g. dexamethasone, H1 antagonist antihistamines e.g. diphenhydramine, and H2 antagonists, e.g. cimetidine, ranitidine. Despite these preventive measures, however, phase II and III studies indicate that minor reactions (flushing and rash) occur in 41-44% of all patients, and that major reactions, necessitating discontinuation of paclitaxel with appropriate first-aid, may occur in approximately 1.5 to 3% of patients (Weiss, R B et al., 1990, *J. Clin. Oncol.* 8, 1263; Eisenhauer, E A et al., 1994, *J. Clin. Oncol.* 12, 2654).

The mechanism of induction of hypersensitivity reactions in response to paclitaxel administration has not yet been elucidated, and research in this area has generated an ongoing debate on the phenomenon. In particular, there is no consensus in the literature regarding two questions: 1) whether the reaction is due to paclitaxel or to the vehicle, Cremophor EL, and 2) whether the phenomenon represents an immunoglobulin E (IgE)-mediated classical type 1 allergic reaction, or it arises as a consequence of direct drug effect on mast cells and/or basophils, causing massive histamine release.

Hypersensitivity reactions to Taxol have been a long-standing concern that exclude some 2% of cancer patients from continuing to receive the drug, while necessitating high-dose steroid and antihistamine pretreatment for the rest of patients who receive this therapy. At present there is no known way to predict the reaction in new patients, or to prevent or control it through specific therapy.

Therefore, a recent report by Essayan et al. (1996, *J. Allergy Clin. Immunol.*, 97, 42) on the prevention of Taxol-induced severe hypersensitivity reactions in a patient by a desensitization protocol similar to that pursued in β-lactam allergy, represents a possible approach to solve this problem. Nevertheless, the immune pathomechanism of hypersensitivity to Taxol and the individual roles that paclitaxel and Cremophor EL play in the reaction remain obscure.

Concerning the pathomechanism, the reaction to Taxol has been referred to in some studies as type I hypersensitivity (Weiss et al., 1990, supra; O'Brien, M. E. R. and Souberbielle, B. E., 1992, *Ann. Clin. Oncol.* 3, 605) primarily on the basis of its rapid clinical course and symptoms. However, conclusive evidence for a role of IgE has never been provided (Essayan et al., 1996, supra; Weiss et al. 1990, supra), and in fact, the phenomenon does not fit into the category of type I allergic reactions because most reactions to Taxol occur during the first treatment, while prior sensitization to an antigen is generally necessary for an IgE response (Rowinsky et al., 1993, supra; Weiss et al., 1990, supra). Also, the high frequency of the mild form of the reaction (41-44%) in the face of the "relative paucity of reactive groups" on paclitaxel (Essayan et al., 1996, supra) is unusual for an IgE-mediated type I reaction. The prevailing view is therefore that the reaction is multifaceted and it is unlikely to be mediated solely by IgE (Rowinsky et al., 1993, supra; Essayan et al., 1996, supra; Weiss et al., 1990, supra). However, the only alternative hypothesis at present, on a direct drug effect on basophils and/or mast cells, still lacks conclusive evidence (Decort, G. et al., 1996, *Anticancer Res.* 16, 317).

The individual roles of paclitaxel and Cremophor EL in the reaction are also a subject of debate. The argument that the phenomenon is due to Cremophor® EL is based on observations that it can cause hypersensitivity reaction in dogs (Lorenz, W. et al., 1977, *Agents Actions* 7, 63) and humans (Sharma et al., 1993, supra; Dye, D. and Watkins, J., 1980, *Br. Med. J.* 280, 1353; Howrie, D. L. et al., 1985, *Drug Intell.*

Clin. Pharm. 19, 425; Lassus, M. et al., 1985, *Proc. Annu. Meet. Am. Soc. Clin. Oncol.* 4, 268; Nolte, H. et al. 1988, *Am. J. Ped. Hematol-Oncol.* 10, 308; Peereboom, D. M. et al., 1993, *J. Clin. Oncol.* 11, 885; Theis, J. G. et al., 1995, *J. Clin. Oncol.* 13, 2508; Fossells, F. V. et al., 1995, *Semin. Oncol.* 22, 22; Mounier, P. et al., 1995, *Therapy* 50, 571). However, other authors, most recently Essayan et al. (1996, supra) contradicted this view and pointed to paclitaxel as the offender.

Similarly, numerous clinical studies in recent years have been performed with liposomal formulations of anticancer drugs and other therapeutic agents. These studies attest to the general safety of i.v. liposomes, as four liposomal drugs entrapping doxorubicin (Doxil®), daunorubicin (DaunoXome®) and amphotericin B (Abelcet® and Ambisome®) are already licensed in several countries, and many others are in advanced clinical trials (Allen, T. M., 1997, *Drugs* 54, 8). Nevertheless, some of the studies (Sculier, J. P. et al., 1986, *J. Clin. Oncol.* 4, 789; Levine, S. J. et al., 1991, *Annals Int. Med.* 114, 664; Ringden, O. et al., 1994, *Lancet* 344, 1156; Laing, R. B. S. et al., 1994, *Lancet* 344, 682; Uziely, B. et al., 1995, *J. Clin. Oncol.* 13, 1777; de Marie, S., 1996, *Leukemia* 10, S93; Dezube, B. J., 1996, In: *Doxil Clinical Series*, Califon, N. J. Gardiner-Caldwell SynerMed, p. 1-8; Alberts, D. S. and Garcia, D. J., 1997, *Drugs* 4, 30) have also revealed a hypersensitivity reaction to liposomes that develops immediately after the start of infusion, and includes symptoms of cardiopulmonary distress, such as dyspnea, tachypnea, tachycardia, hypotension, chest pain and back pain. Unlike IgE-mediated (type I) allergy, the reaction to liposomes arises at the first exposure to the drug without prior sensitization, and the symptoms usually lessen or disappear upon later treatments. Because of these unusual features, the reaction has recently been termed "pseudo-allergic" (Alberts and Garcia, 1997, supra). The frequency of such reactions among 705 patients treated with Doxil was 6.8% (Dezube, 1996, supra) which is comparable with the incidence rate reported in other liposome trials (Levine, S. J. et al., 1991, supra; Ringden et al., 1994, supra; Uziely, B. et al., 1995, supra; deMarie, S., 1996, supra; Alberts and Garcia, 1997, supra). As the mechanism of the phenomenon is not understood, it is impossible at present to anticipate or specifically treat some 0.9% of patients who develop a severe, life-threatening reaction that precludes further treatment (Dezube, 1996, supra).

It is known that certain liposomes can activate the complement system (Szebeni, J., 1998, *Crit. Rev. Ther. Drug Carrier Syst.* 15, 57), and that complement activation can lead to cardiovascular and pulmonary adverse responses very similar to those described above (Marceau, F. et al., 1987, *Immunopharmacol.* 14, 67; Hammerschmidt, D. E. et al., 1980, *Lancet* 3, 947; Moore, F. D., 1994, *Adv. Immunol.* 56, 267). Thus, we wished to test the hypothesis that complement activation plays a causal role in the cardiopulmonary reaction to i.v. liposomes. We chose the pig as animal model as an earlier study in our laboratory demonstrated that i.v. administration of cholesterol-containing liposomes in miniature pigs elicited a severe anaphylactoid reaction that was associated with intense hemodynamic changes (Wassef, N. M. et al., 1989, *J. Immunol.* 143, 2990). It was proposed that the reaction was due to complement activation, however, direct, conclusive evidence regarding the causal role of complement was not available previously.

Therefore, there is a need to determine the mechanism behind the hypersensitivity reactions described above such that a method for inhibiting said hypersensitivity can be applied.

SUMMARY OF THE INVENTION

The present invention satisfies the need discussed above. We provide evidence that Cremophor EL or liposomes cause significant complement (C) activation in human sera at a frequency that is comparable to the overall incidence of minor plus major hypersensitivity reactions to Taxol or liposomes in cancer patients. We demonstrate that the C reaction involves both the classical and the alternative pathways, and that it can efficiently be inhibited by soluble C receptor type 1 (sCR1). Based on a remarkable structural similarity between molecules present in Cremophor EL and certain nonionic block copolymers, which activate C, we provide a hypothesis on the mechanism of C activation by Cremophor EL.

A possible connection between C activation and hypersensitivity reactions to Cremophor EL was considered in 1980 in a case report by Huttel et al., (Huttel, M. S. et al., 1980, *Br. J. Anaesth.* 52, 77) in which the authors described an adverse reaction to Stesolid MR (diazepam with Cremophor as solvent) that was associated with the conversion of C3, a native complement component, to the anaphylatoxin C3a immediately following the reaction. Based on this observation and the comparable frequency of adverse reactions to Stesolid MR, althesin and propandid, which are all dissolved in Cremophor EL, Hüttel et al. suggested that Cremophor-induced C activation could play a role in these reactions (Huttel, M. S. et al., 1980, *Br. J. Anaesth.* 52, 77). However, to our knowledge, the concept has not gained confirmation and/or broad recognition subsequently.

The present experiments were initiated as it came to our attention that the mentioned symptoms of hypersensitivity to Taxol, too common to be explained by classical type I hypersensitivity, are also typical of C activation observed in patients at the start of extracorporeal circulation, such as hemodialysis, cardiopulmonary bypass and plasmapheresis (Cheung, A. K., 1984, *Plasma Ther. Transf.* 5, 505; Skroeder, N. R., 1994, *Artif. Organs* 18, 880). Like the binding of allergens to IgE on the surface of mast cells and basophils, the anaphylatoxins C3a and C5a can trigger the release of histamine, prostaglandins, leukotrienes and many other vasoactive mediators from these cells (Marceau, F. et al., 1987, *Immunopharmacol.* 14, 67). Through this cascade of secondary mediators, C activation is known to provide huge amplification of effector immune responses. Thus, this mechanism would explain a puzzling feature of Taxol hypersensitivity, i.e. that infusion of only minute amounts of the drug can precipitate a strong immediate reaction despite prior exposure to the drug. It should be mentioned in this regard that C has been known to be involved in the effector arm of antibody-mediated type II and type III allergic reactions, which are clearly not applicable for the case of Taxol.

Therefore, it is one object of the present invention to provide a method for inhibiting or preventing unwanted side effects caused by a pharmaceutical solvent or carrier containing amphiphilic molecules such as polyethoxylated oils or derivatives thereof, such as Cremophor EL or liposomes, employing a complement activation inhibitor, separately or in conjunction with such solvent or carrier.

In an embodiment of the method of the present invention, the complement activation inhibitor is employed in conjunction with a pharmaceutical composition including a pharmaceutical, such as paclitaxel, and a solvent containing C-activating molecules, such as present in polyethoxylated castor oil (Cremophor EL), or C-activating drug carriers such as liposomes, or derivatives of different liposomal structures.

It is another object of the present invention to provide a pharmaceutical composition which includes a pharmaceutical comprising a solvent or carrier containing amphiphilic molecules such as polyethoxylated oils or a derivative thereof; and a complement activation inhibitor.

BRIEF DESCRIPTION OF THE DRAWINGS

These and other features, aspects, and advantages of the present invention will become better understood with reference to the following description and appended claims, and accompanying drawings where:

FIG. 4. Inhibition of Cremophor EL-induced complement activation by soluble complement receptor type 1 (sCR1): dose activity relationship. Cremophor EL (8.8 mg/ml) was incubated with the serum of a healthy subject in the presence of the indicated concentrations of sCR1. Serum levels of SC5b-9 were measured by enzyme-linked immunoasorbent assay, as described. Bars=mean values with 95% confidence interval, obtained from triplicate wells. The rise of SC5b-9 relative to PBS was statistically significant at *, P=0.0006 and **, P=0.002 (Student's two-sample t test, two-tailed).

FIGS. 5A and B. Similarities between complement-activating block copolymers and Cremophor EL in molecular structure and supramolecular organization. A) The triblock copolymer L101 contains 6 hydrophilic oxyethylene (polyoxyethylene, POE) units flanking a central hydrophobic core of 57 oxypropylene (polyoxypropylene, POP). L121 consists of POE and POP arranged in a similar sandwich structure, with the hydrophilic and hydrophobic blocks consisting of 7 to 70 units, respectively (O'Dwyer, P. J. and Weiss, R., 1984, *Cancer Treat. Rep.* 68, 959; Athanassiou, A. E. et al., 1988, *J. Clin. Oncol.* 6, 1204). As illustrated, these molecules are oriented at the water-oil interface in such manner that the hydrophilic blocks form a continuous adhesive layer on the surface of the oil phase, which was shown to bind plasma proteins and activate complement (O'Dwyer, P J and Weiss, R., 1984, *Cancer Treat. Rep.* 68, 959; Athanassiou, A E et al. 1988, *J. Clin. Oncol.*, 6, 1204).

B) Hypothetical positioning of different amphiphilic molecules present in Cremophor EL at the water-oil interface. The circled letters A-H assign the molecules to the formulas presented in FIG. 1. The cross-hatched areas represent the hyrophobic (oil) phase, in which the hydrophobic fatty acid (FA) parts of Cremophor molecules immerse. Because the width and chemical composition (POE) of the hydrophilic protein-binding layer on the surface of the oil phase are comparable in the case of block copolymers and Cremophor EL, we hypothesize that the reported C activation by L101 and 121 (Hunter, R L and Bennett, B., 1984, *J. Immunol.*, 133, 3167; Hunter, R L and Bennett, B., 1987 *Prog. Leuk. Biol.* 6, 181) provides a model for C activation by Cremophor EL.

FIG. 6. Hemodynamic changes induced by liposomes in pigs. Typical curves from 3 pigs injected with the liposome boluses. PAP, pulmonary arterial pressure; PVR, pulmonary vascular resistance; SAP, systemic arterial pressure; SVR, systemic vascular resistance. Experimental details and calculation of SVR and PVR are described in Methods. Different symbols designate different pigs.

Figure 7:
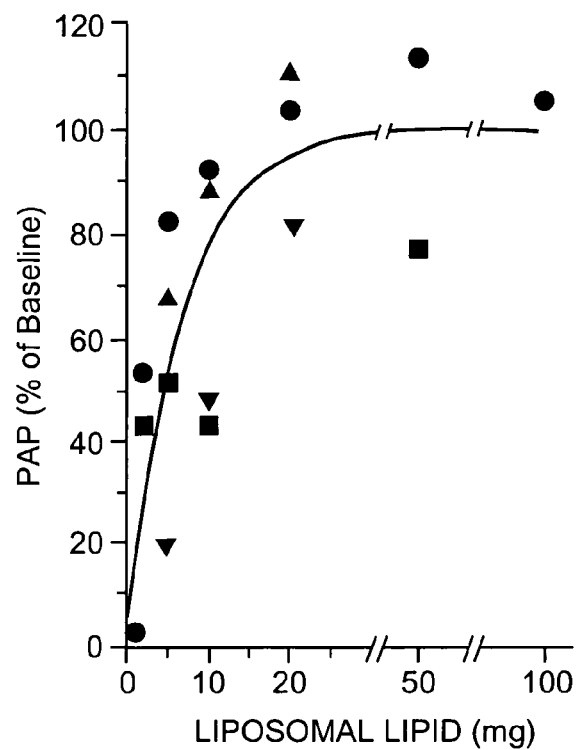

FIG. 7. Dose-response relationship between liposomal lipid and PAP. Data compiled from 4 different pigs, indicated by different symbols. Fitted is a monoexponential curve in the following form: PAP=100.2×(1−e−0.15×L), where L is lipid dose in mg. $ED_{50}$=4.5±1.4 mg; $R^2$=0.78; Durban-Watson value=0.85; error variance constant (heteroscedasticity) P=0.6 (Stahl, G. et al., 1997, *Am. J. Physiol.* 272, C1821; Martin, S. E. et al., 1988, *Circ. Res.* 63, 483).

Figure 8:
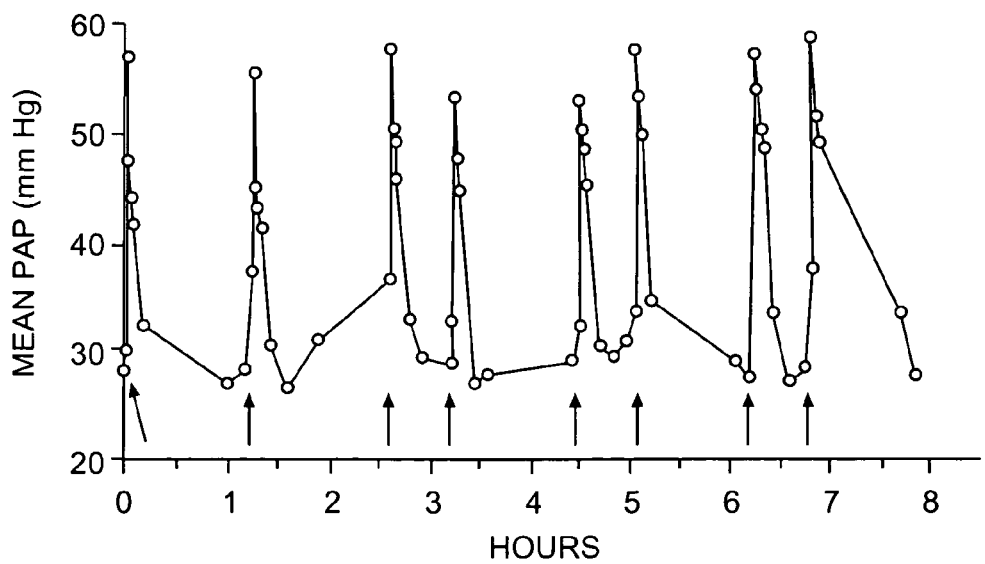

FIG. 8. PAP responses to repetitive liposome injections. A pig was injected i.v. with the standard liposome boluses 8 times at the indicated time points, and the changes in PAP were recorded. The arrows indicate the time of injections.

Figure 9A:
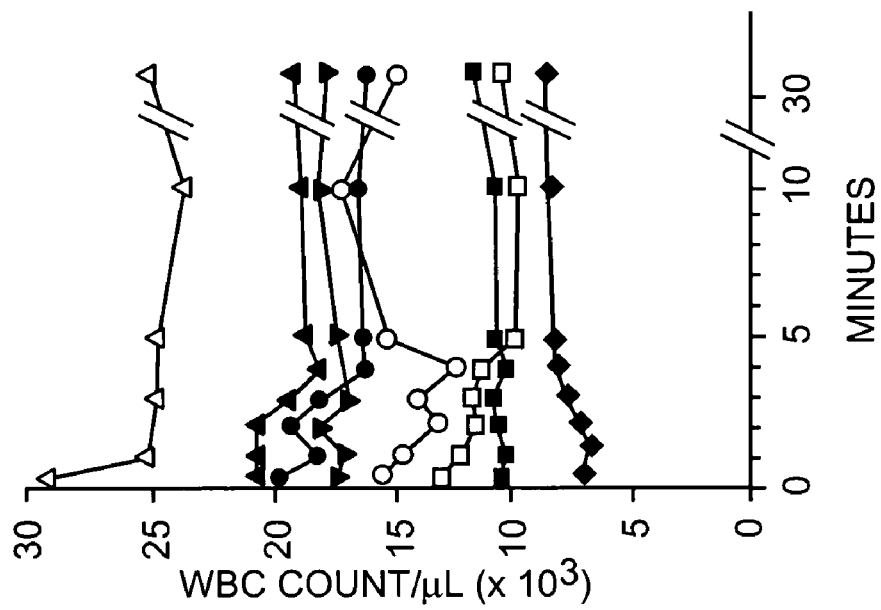
Figure 9B:
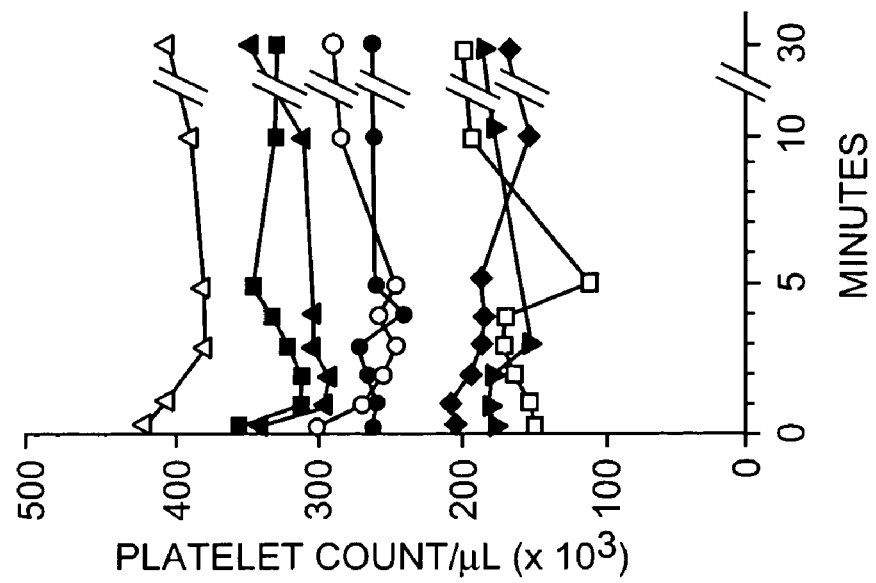

FIG. 9. Liposome-induced changes in platelet (A) and WBC (B) counts. Cell counts were determined as described in the Methods, before the injection of a standard liposome bolus (zero minute), and at different times thereafter, as indicated. Different symbols designate individual pigs.

Figure 10A:
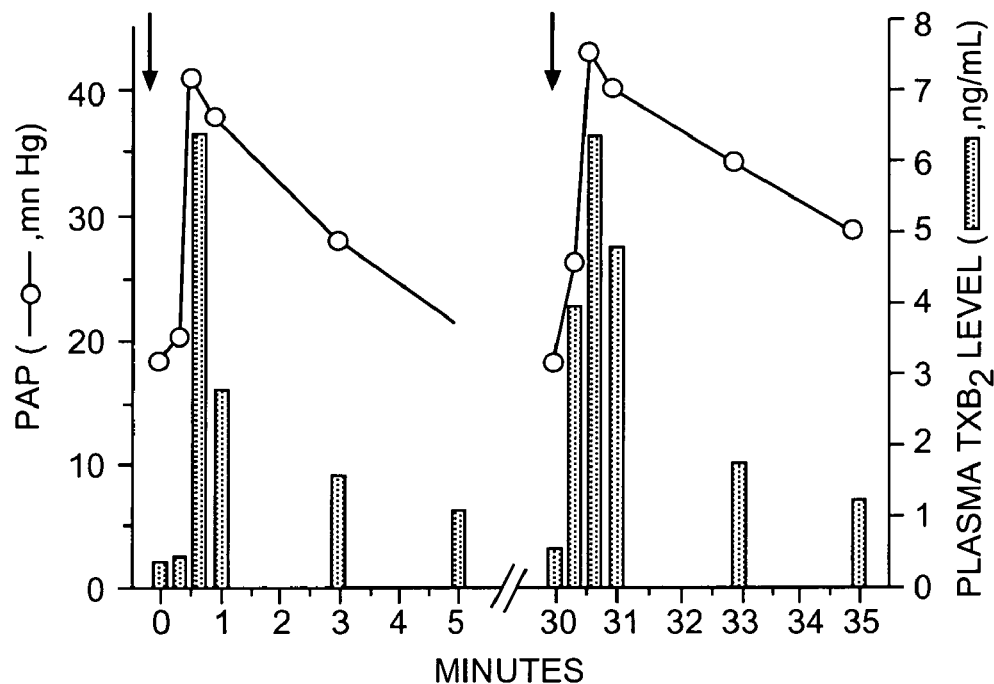
Figure 10B:
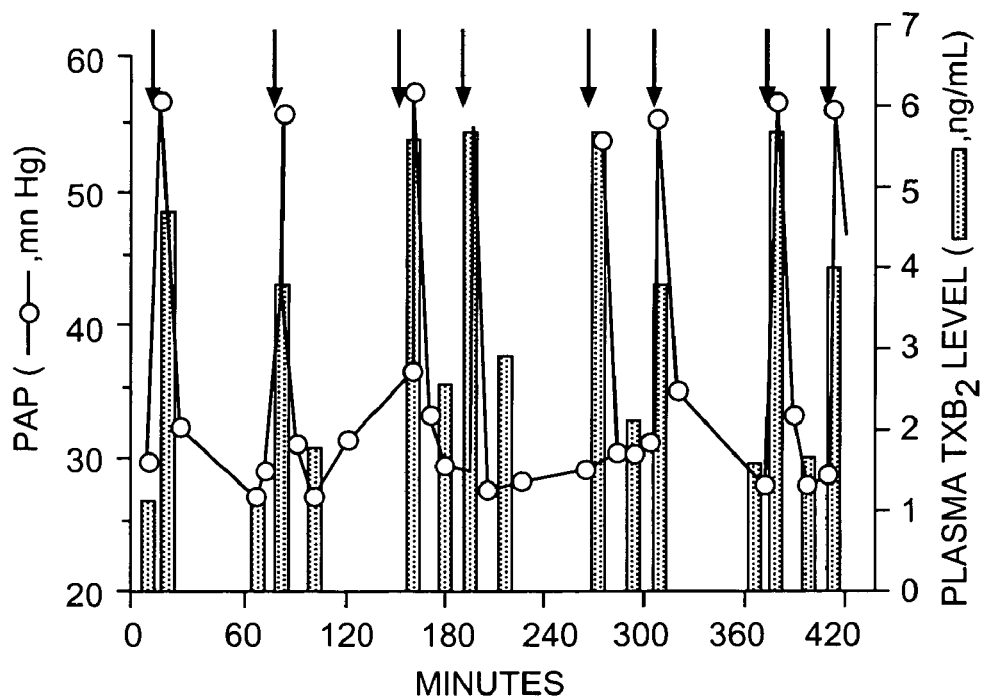

FIG. 10. Time course of liposome-induced changes in plasma $TXB_2$ and PAP. Pigs were repetitively injected with standard liposome boluses, and the changes in PAP (circles) and plasma $TXB_2$ (bars) were plotted as a function of time for the first two injections in one pig (A and B), or over hours in another pig (C).

Figure 11:
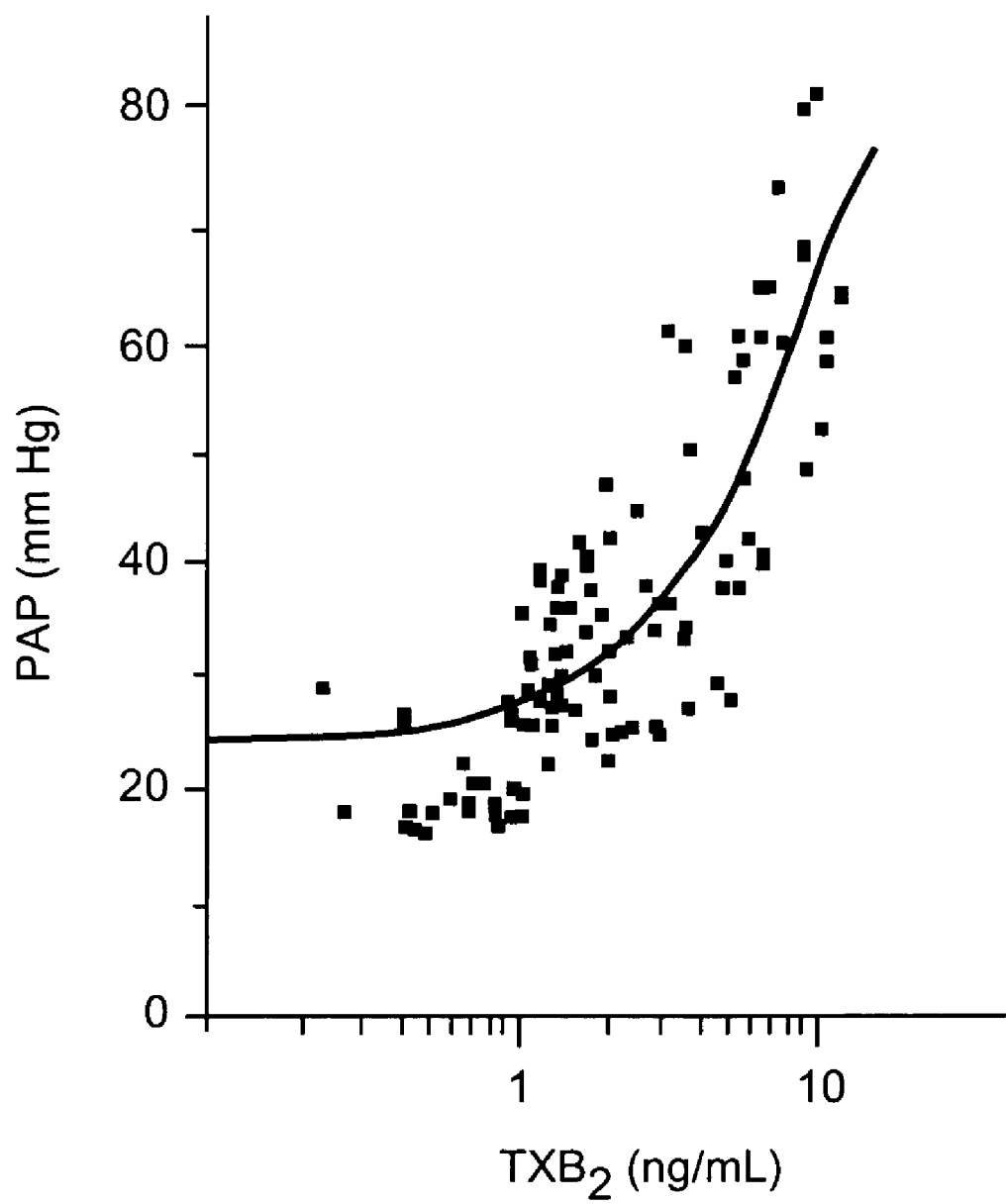

FIG. 11. Dose-response relationship for PAP as a function of plasma $TXB_2$ before and at different times following injection of various liposomes. Data (n=96) compiled from 7 pigs.

The best fit is a logistic curve in the following form: $Ln((PAP/PAPmax)/(1-PAP/PAPmax))=-0.89+0.24\times[TXB_2]$, where PAPmax is 82 mm Hg and $[TXB_2]$ is plasma $TXB_2$ level in ng/mL. $R^2=0.67$, P (of coefficients) $<10^{-4}$, Durban-Watson value=2.2, Wilk-Shapiro error variance constant=0.96 (Chatterjee, S. et al. *Regression Analysis by Example*, Newy York: Wiley, 1977; Kang, Y. H. et al., 1992, *Pflugers Arch.* 421, 188). The latter parameters indicate appropriate model specification, i.e., that $TXB_2$ was the main, if not sole predictor variable of PAP. The 33% unexplained variability of PAP ($R^2=0.67$) may be due to inter-animal variation plus measurement errors.

FIG. 12. The effects of complement inhibitors and indomethacin on liposome-induced pulmonary hypertension. Panel A presents the standard liposome-induced changes in PAP before and at different times after the administration of the indicated inhibitors, each in a different animal. Panel B shows post-inhibitor PAP responses, expressed as % of pre-inhibitor response, at the time of maximal inhibition in 4 pigs in each inhibitor group. Inhibitors were injected in the jugular vein in 4-8 mL PBS, at the following doses: GS1, 1.6 mg/kg (squares), sCR1, 0.2 mg/kg (open circles) and 2 mg/kg (closed circles); indomethacin, 5 mg/kg (triangles). A comparison of pre- and post-inhibitor PAP showed significant inhibitory effect for all 3 drugs ($P<0.01$ by Student's paired t-test, two-tail).

Figure 13A:
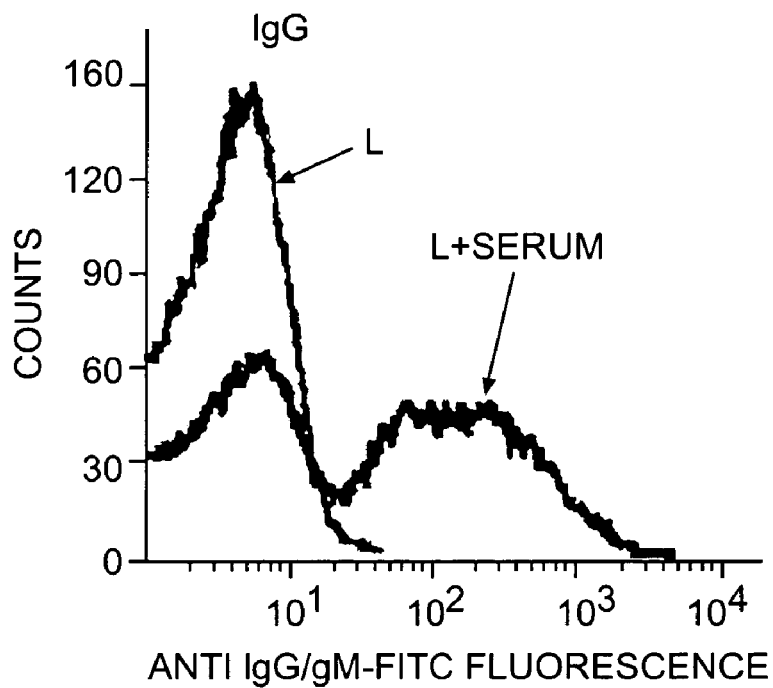
Figure 13B:
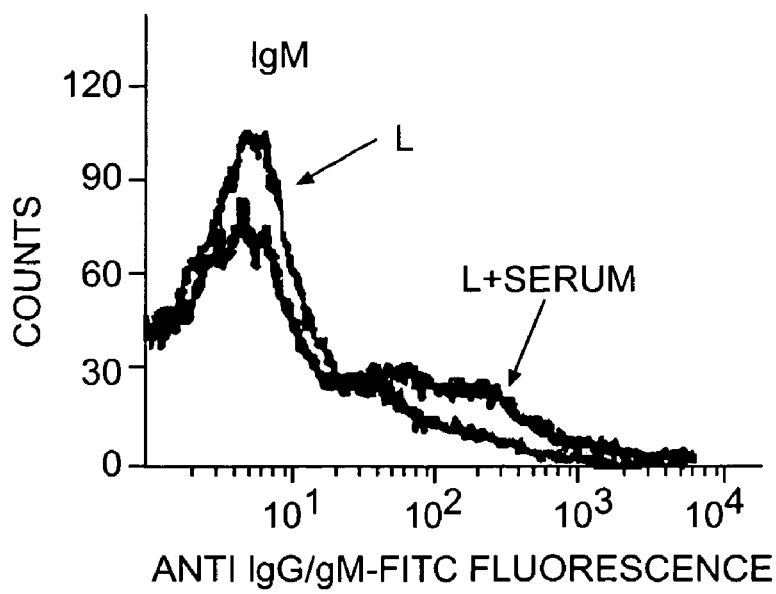

FIG. 13. Binding of porcine IgG and IgM to liposomes in vitro. Following incubation with PBS or pig serum, liposomes were fixed, washed, incubated with antibodies against porcine IgG or IgM and counterstained with FITC-conjugated $F(ab)_2$, as described in the Methods. For each liposome sample 10,000 data points were acquired. Vesicles stained with an unrelated polyclonal antibody showed no greater fluorescence than those incubated with PBS (data not shown). An independent experiment gave essentially identical results.

Figure 14:
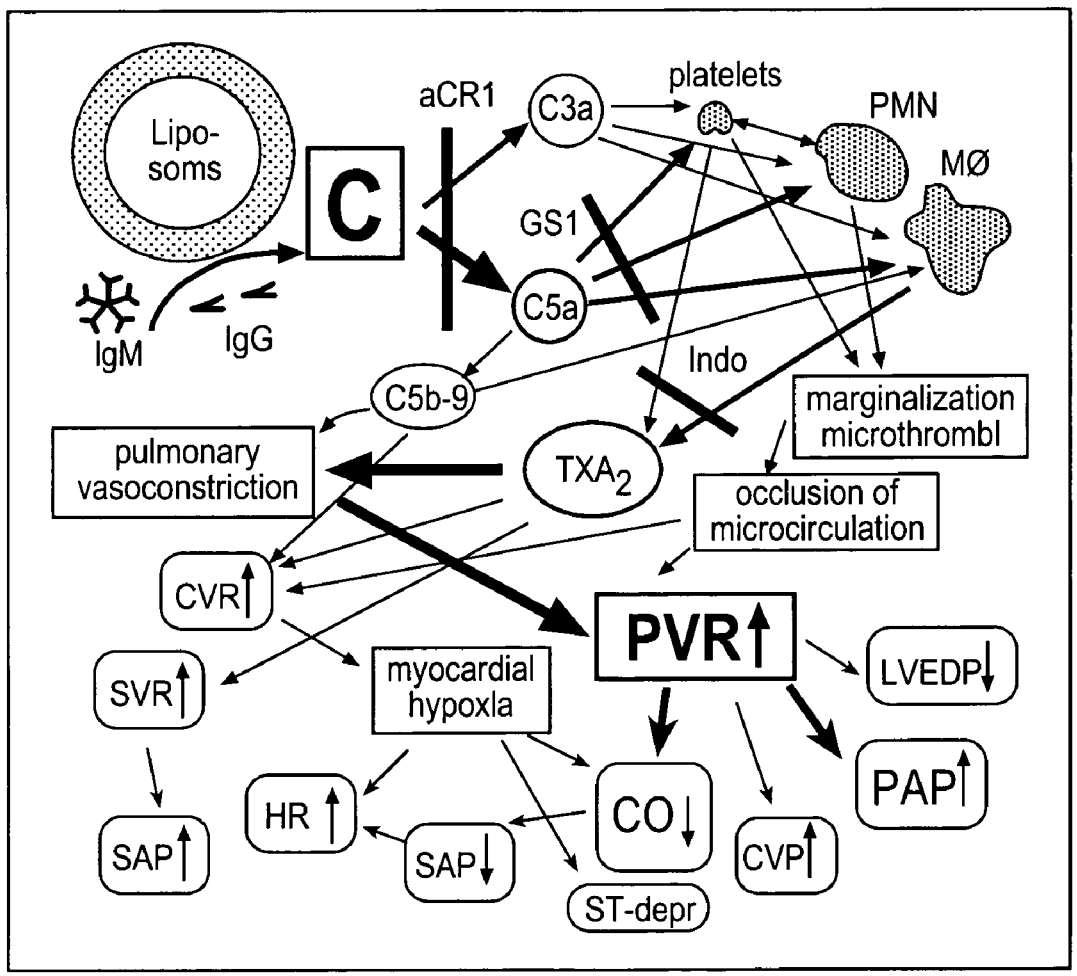

FIG. 14. Mechanism of liposome-induced hemodynamic changes in pigs. The scheme also shows the sites where sCR1, GS1 and indomethacin exert their inhibitory effects. The abbreviations used only in this figure are: C, complement; HR, heart rate; MØ, macrophage; Indo, indomethacin; CVR, coronary vascular resistance; ST-depr, ST-segment depression.

Figure 15:
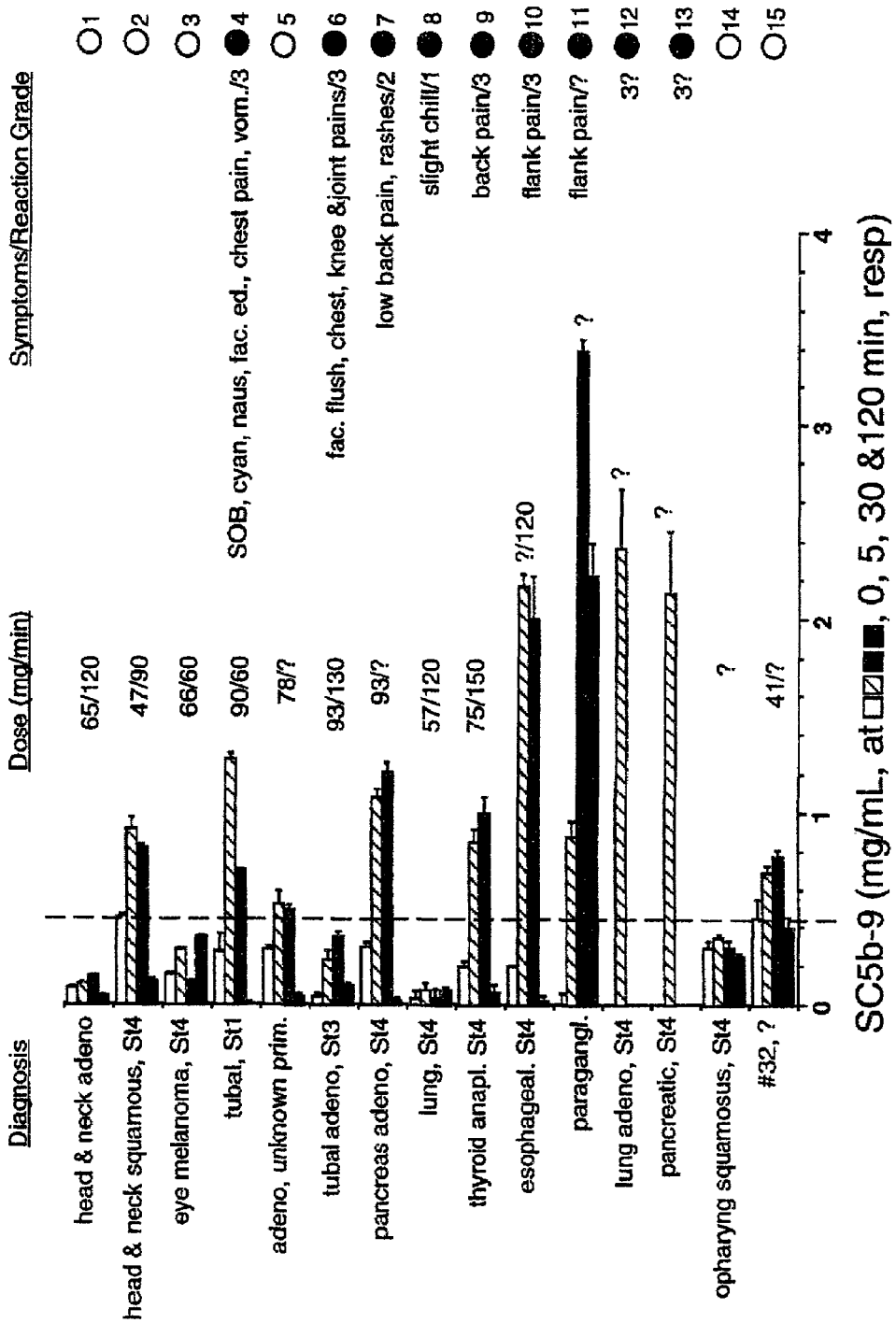

FIG. 15. Correlation between complement activation and clinical symptoms of hypersensitivity to Doxil. 1-2 ml blood samples were taken into EDTA-containing collection tubes before, and at 10, 30, and 120 minutes after the start of Doxil infusion. Blood was then centrifuges at 4° C., and the plasma was stored at $-70°$ C. until determination of SC5b-9 level by ELISA (Quidel, San Diego, Calif.). Patients were observed for at least 15-30 minutes into the infusion and any subjective or objective signs of hypersensitivity reaction were recorded and scored.

DETAILED DESCRIPTION

The present invention relates to a method for inhibiting or preventing unwanted side effects caused by a pharmaceutical solvent or delivery system containing amphiphilic molecules, such as those present in polyethoxylated castor oil or derivatives thereof, or in liposomes, employing a complement activation inhibitor.

In order to better understand the present invention, the following description of the complement system is provided.

The Complement System

The C system represents the nonspecific arm of humoral immunity, which provides the first line of defense against microbial infections or other harms caused by alien agents. For a review of the molecular details and biological consequences of complement activation, please see Halkier, T., Overview of the complement system, in *Mechanisms on Blood Coagulation*, Cambridge University Press, Cambridge, 1991, 163; and Morgan, B. P., Physiology and pathophysiology of complement: Progress and trends, *Crit. Rev. Clin. Lab. Sci.* 32, 265, 1995.

Briefly, the complement system is a group of some 30 plasma glycoproteins that constitutes 10 percent of the globulins in the normal serum of humans (Hood, L. E. et al. 1984, *Immunology*, 2d Edition, The Benjamin/cummings Publising Co., Menlo Park, Calif., p. 339). Complement plays an important role in the mediation of immune and allergic reactions. The activation of C components leads to the generation of a group of factors, including chemotactic peptides that mediate the inflammation associated with complement-dependent diseases. The sequential activation of the complement system may occur via three pathways: 1) the classical pathway involving C1q as C ligand and antibodies, or other membrane binding sites as activators; 2) the "lectin" pathway, involving mannose binding lectin (MBL) as initiator ligand that binds to carbohydrate receptors on activating surfaces, and 3) the alternative pathway, whereby C3 is activated following direct deposition on activator surfaces. The activities mediated by activated complement proteins include lysis of target cells, chemotaxis, opsonization, stimulation of vascular and other smooth muscle cells, degranulation of mast cells, increased permeability of small blood vessels, directed migration of leukocytes, and activation of B lymphocytes, macrophages and neutrophils.

During proteolytic cascade steps, biologically active peptide fragments, the anaphylatoxins C3a, C4a, and C5a are released from the third (C3), fourth (C4) and fifth (C5) native complement components (Hugli, T. E. *CRC Crit. Rev. Immunol.* 1981, 1, 321; Bult, H. and Herman, A. G. *Agents Actions* 1983, 13, 405). C3b, which binds to target immune complexes of foreign substances and marks them for destruction or clearance, is generated from its precursor C3 by proteolytic enzymes collectively designated C3 convertase. One form of C3 convertase is generated in the classical pathway by the association of the proteins C4b and C2a. The other form is generated in the alternative pathway by association of C3b and Bb. Both C3 convertases can associate with an additional C3b subunit to form the C5 convertases, C3bBbC3b and C4bC2aC3b, both of which are active in the production of the C5-C9 membrane attack complex which can cause cell lysis, and in the production of C5a, a major pro-inflammatory agent.

The effects of the complement system can be inhibited by two general mechanisms. The first mechanism is generally reversible, facilitating the dissociation of the C3 convertases, i.e. C3b from Bb and C4b from C2a. Facilitation of dissociation is sometimes known as decay acceleration. The dissociation may also involve reversible binding of the antagonist proteins to C3b or C4b components, thus preventing their reassociation. The other mechanism, which is an irreversible inactivation process, results from proteolytic cleavage of the C3 convertase components C3b or C4b by the serine protease factor I. This proteolytic cleavage occurs only in the presence of a cofactor. Both general regulatory mechanisms, the facilitation of dissociation of C3b and C4b and the inactivation of C3b and C4b through cleavage by factor I, also apply to the inhibition of the alternative pathway C5 convertase (C3bBbC3b) and the classical pathway C5 convertase (C4bC2aC3b).

The proteins encoded by a region of the genome which is designated the "regulators of complement activation" (RCA) gene cluster are involved in both of the foregoing mechanisms. At least six proteins are encoded by this region. The reversible binding to C4b or C3b to dissociate the C3 convertases is effected by two plasma proteins designated C4 binding protein (C4bp) and factor H, and by two membrane proteins designated decay acceleration factor (DAF) and complement receptor 1 (CR1). Reversible binding to C4b is effected by C4bp, DAF and CR1 while reversible binding to C3b is effected by factor H, DAF, and CR1.

The irreversible inactivation of the C3 convertases resulting from proteolytic cleavage of convertase components C3b or C4b by the enzyme factor I can occur by virtue of cofactor activity effected by the above-mentioned factor H and C4bp in the plasma and by CR1 and membrane cofactor protein (MCP) at the cell surface. Cofactor activity for cleavage of C3b is effected by factor H, CR1 and MCP while cofactor activity for cleavage of C4b is effected by C4bp, CR1 and MCP. It is also possible that the sixth protein, complement receptor 2 (CR2), has this cofactor activity at the cell surface.

The term "amphiphilic molecules" is meant to include molecules which have both hydrophilic and hydrophobic parts, causing self-assembly in different multimolecular structures, such as micelles or planar sheets, called membranes.

In general, dugs which are poorly soluble in water-based solvents necessitate the addition of emulsifiers to the solvent. Such emulsifiers usually contain amphiphilic molecules. Examples of such emulsifiers are polyethoxylated oils and derivatives thereof, nonionic detergents such as Tween compounds and derivatives thereof known to persons in the art.

The term "polyethoxylated oil" includes oils, such as castor (ricinus) oil (i.e. oil comprised of a mixture of triglicerides with 90 recinoleic acid-ester content), reacted with ethylene oxide at heat and pressure.

Examples of solvents including polyethoxylated oils or derivatives thereof suitable for use herein include, but are not limited to, the Cremophor family of emulsifiers comprising different grade polyethoxylated castor oil, including Cremophor EL, other amphiphilic detergents, lipids and phospholipids that form micelles, particles, membranes and other types of supramolecular structures that share the feature of creating continuous surfaces in water to which plasma proteins can bind.

The term "Cremophor" as employed herein refers to an amphiphilic detergent composed of polyethoxylated castor oil that may or may not contain alcohol, such as ethanol and is marketed by BASF and as Etocas by Croda, U.K. Cremophor EL is produced by reacting castor oil with ethylene oxide at heat and pressure. The product consists of a complex mixture of unmodified castor oil and a large variety of polyethylene glycols, polyethoxylated glycerol, polyethoxylated fatty acids and mono-, di- and triesters of glycerol that is polyethoxylated to different degrees (Müller K., 1996, *Tenside* 3, 37).

The term "liposomes" as employed herein refers to amphiphilic molecules which have formed membrane vesicles tightly enclosing an internal water space that may or may not contain drugs or other active agents. The principle amphiphilic molecules in liposomes comprise phospholipids. Phospholipids are composed of fatty acyl side chains that are saturated or unsaturated, that are esterified to hydroxyl groups of a glycerol molecule. One hydroxyl group on glycerol is esterified with phosphate. In some phospholipids, the phosphoric acid which is esterified is also esterified to a hydroxyl group on a hydrophilic compound such as ethanolamine, or serine, choline, or glycerol (Darnell, J. et al. (eds.), 1986, In: *Molecular Cell Biology*, Scientific American Books, New York, N.Y., p. 92).

Pharmaceuticals which may be present in the pharmaceutical compositions of the invention carried in the solvent or emulsifier containing amphiphilic molecules such as polyethoxylated oils or derivatives thereof include, but are not limited to, all drugs that are poorly soluble in water-based solvents and necessitate the addition of emulsifiers to the solvent such as cyclosporine A, Vitamin K (phytonadione, konakion), teniposide, didemnin E, miconazole, diazepam, althesin, taxol, echinomicin, propandid, steroids, multivitamin products, and the like. Drugs carried in liposomal formulations include, but are not limited to, anticancer drugs such as doxorubicin, daunorubicin, and amphotericin B.

Any drug or active agent, can be carried in liposomes or liposome vesicles such as agents with therapeutic and/or diagnostic value such as antifungal or anticancer drugs, regardless of their chemical nature, such as proteins, for example, hemoglobin, peptides, amino acids, carbohydrates, oligo- and polynucleic acids or any type of organic or inorganic atoms or molecules.

The above pharmaceuticals are known in the art and are employed in amounts as set out in the Physician's Desk Reference (PDR), 1998. If a particular pharmaceutical is not set out in the PDR, it will be employed in amounts set out in publications and/or patents relating thereto.

Complement activation inhibitors which may be employed herein include agents that inhibit at any stage the autocatalytic proteolysis involved in C activation, either by blocking the binding of C proteins to activator molecules or surfaces, or their interaction with each other, or the enzyme activity of C3 and C5 convertases. Complement inhibitors also include molecules that interfere with the activity of the membrane attack, or terminal complex (C5b-9, TCC), as well as with the activities of anaphylatoxins (C3a, C4a, C5a) at any stage or level, including their binding to specific cell surface receptors and subsequent signal transduction. Such complement activation inhibitors include antibodies, monoclonal, polyclonal and Fab fragments which are found to inhibit compelment activation, chimeric complement inhibitor proteins, sCR1 (Weisman, H. F. et al., 1990, *Science* 249, 146), GS1, an anti-C5a monoclonal antibody (Stahl, G. L. et al., 1997, *FASEB J.* 11, A331), Factor H, Factor I, C1qInh, soluble forms of DAF, MCP, complestatin, and anti-C5a, sythetic peptide analogs of the C-terminal part of C3, CAB-2, Indel proximal peptides.

Organic compounds which inhibit complement include, but are not limited to, amino acids (Takada, Y. et al. *Immunology* 1978, 34,509); diamines; phosphonate esters (Becker, L. *Biochem. Biophy. Acta* 1967, 147, 289); polyanionic substances (Conrow, R. B. et al. *J. Med. Chem.* 1980, 23, 242); sulfonyl fluorides (Hansch, C. and Yoshimoto, M. *J. Med. Chem.* 1974, 17, 1160, and references cited therein); sulfonated aromatic compounds, polynucleotides (DeClercq, P. F. et al. *Biochem. Biophys. Res. Commun.* 1975, 67, 255); primaric acids (Glovsky, M. M. et al. *J. Immunol.* 1969, 102, 1); porphines (Lapidus, M. and Tomasco, *J. Immunopharmacology* 1981, 3, 137); several antiinflammatories (Burge, J. J. et al. *J. Immunol.* 1978, 120, 1625); phenols (Muller-Eberhard, H. J. 1978 in *Molecular Basis of Biological Dearadative Processes*, Berlin, R. D. et al., eds. Academic Press, New York, p. 65); and benzamidines (Vogt, W. et al. *Immunology* 1979, 36, 138); and compound K-76COOH described in U.S. Pat. No. 5,506,247 to Sindelar et al. Some of these agents express their activity by general inhibition of proteases and esterases. Others are not specific to any particular intermediate step in the complement pathway, but rather, inhibit more than one step of complement activation. Examples of the latter include the benzamidines, which block C1, C4 and C5 utilization (Vogt, W. et al. *Immunology* 1979, 36, 138) For recent reviews of complement inhibitors please see Liszewski, M. K. and Atkinson, J. P., 1998, *Exp. Opin. Invest. Drugs* 7, 323 and Makrides, S. C., 1998, *Pharmacol. Rev.* 50, 59.

Any compound which is found to inhibit complement activity can be used. Compounds can be assayed for their ability to inhibit complement activation. Such assays are known to persons with skill in the art and include but are not limited to the following in vitro tests for the ability to inhibit complement system activation or to selectively inhibit the generation of complement-derived peptides:

(i) measurement of inhibition of complement-mediated lysis of red blood cells (hemolysis);

(ii) measurement of ability to inhibit formation of C5a and C5a des Arg (a less potent but still active C5a without the carboxy-terminal arginine) and/or measurement of ability to inhibit formation of C3a and C3a des Arg.

(iii) inhibition of alternative pathway mediated hemolysis.

Those compounds which are demonstrated to have significant complement-inhibiting activity can be used in the present invention.

The complement activation inhibitor will be employed in the solvent formulation and pharmaceutical formulations of the invention in a weight ratio to the solvent of within the range of from about 0.0001:1 to about 10,000:1, preferably from about 0.002:1 to about 1000:1.

The formulations of the invention may also include additional solvents and/or carrier materials and/or extenders such as alcohols, e.g. ethanol, water, sodium chloride or dextrose or other pharmaceutically acceptable solvents used for systemic, including oral or parenteral, administration.

In carrying out the method of the present invention, the complement activation inhibitor in combination with the amphiphilic solvent or carrier and pharmaceutical therein, or the complement inhibitor alone, may be administered to mammalian species, such as monkeys, dogs, cats, rats, humans, etc. Methods of adminstration include but are not limited to oral, intradermal, transdermal, intravenous, subcutaneous, intramuscular, intraperitoneal, and intranasal routes. Such administration can be done in either bolus or repeat doses or continuously by infusion for instance.

With regard to the dosage of complement inhibitor, where the drug is administered by catheter from about 0.1 to about 30 mg/kg/dose and preferably from about 0.5 to about 25 mg/kg/dose will be employed. From 1 to 5 doses per day will be required.

Where the complement inhibitor alone or in combination with any of the other components of the formulation of the invention is to be administered by angiography or intracoronary injection, it (or the combination) will be formulated in a conventional vehicle, such as distilled water, saline, Ringer's solution, or other conventional carriers.

The complement inhibitor alone or in combination with any of the other components of the formulation of the invention may also be incorporated in a conventional dosage form, such as a tablet, capsule or elixir or injectable. The above dosage forms will also include the necessary carrier material, excipient, lubricant, buffer, antibacterial, bulking agent (such as mannitol), anti-oxidants (ascorbic acid of sodium bisulfite) or the like. Parenteral dosage forms are preferred, although oral forms may be satisfactory as well.

The complement inhibitor may be employed in a separate dosage form from any of the other components of the formulation of the invention such as two separate injections or the two or three may be employed in a single dosage form, such as a single injection.

With regard to such systemic formulations, where the complement inhibitor is to be employed alone, single or divided doses of from about 1 to about 10,000 mg, preferably from about 2 to about 2000 mg/one to four times daily, may be administered in systemic dosage forms as described above.

The complement inhibitor alone or with any of the other components of the formulation of the invention may be administered prior to, during, or after administration of the carrier and pharmaceutical or solvent/and or pharmaceutical.

A pharmaceutical kit comprising one or more containers filled with one or more of the complement inhibitors can be included along with containers containing the pharmaceutical and solvent or carrier and other necessary reagent or reagents for mixing or dissolving any of the components of the kit.

This invention can be better understood by referring to the following examples which are given for illustrative purposes only and are not meant to limit the invention.

The following MATERIALS AND METHODS were used in the examples that follow.

Drugs and Reagents

Figure 1:
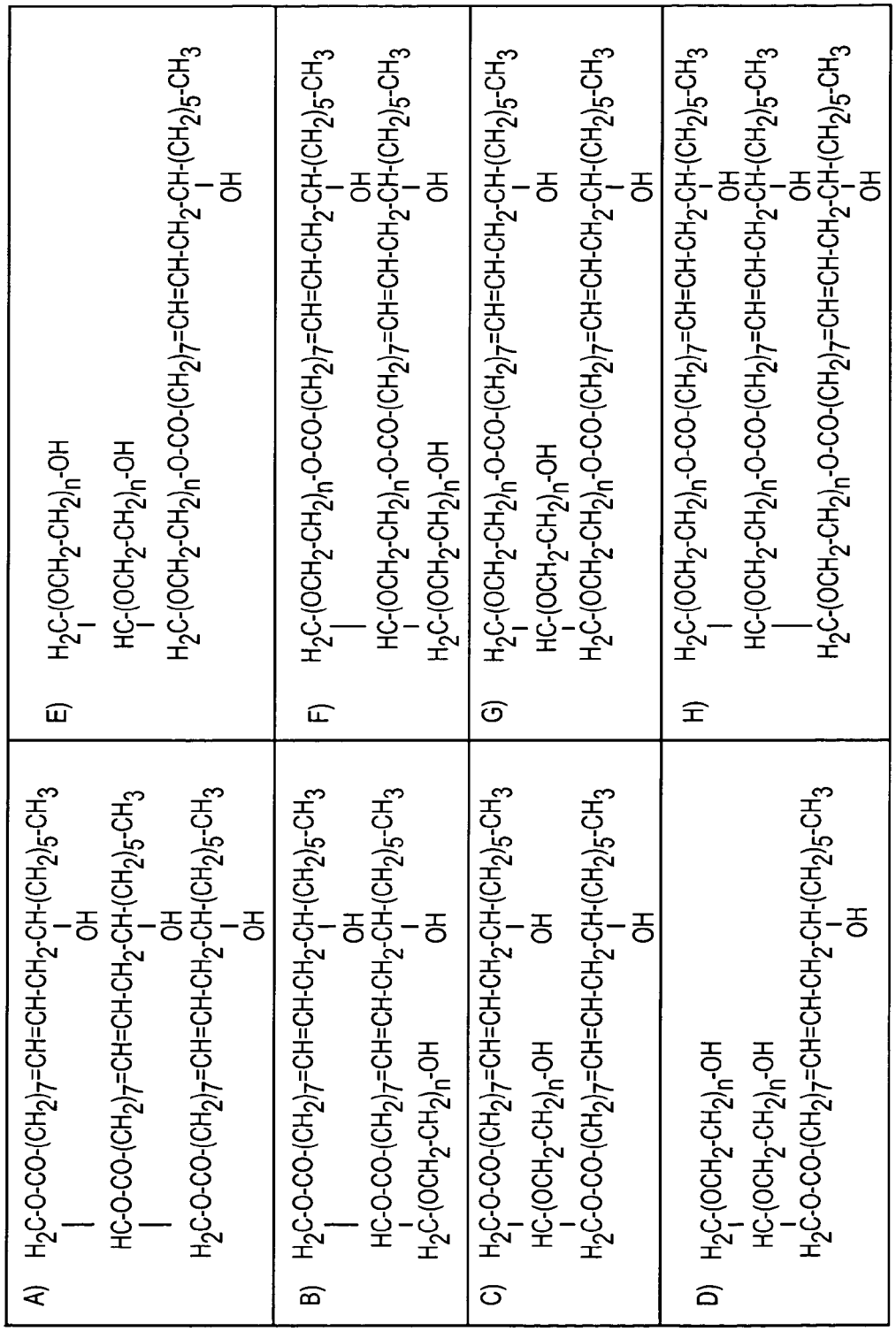
FIGS. 1A-H. The chemical structure of Cremophor EL. A, castor (ricinus) oil, the raw material of Cremophor EL. The structure shows the most abundant (90%) triglyceride in castor oil, in which glycerol is esterified by ricinoleic (12-hydroxy-9-octadecenoic) acid. Cremophor EL is produced by reacting castor oil with ethylene oxide at heat and pressure. The product consists of a complex mixture of unmodified castor oil and a large variety of polyethylene glycols, polyethoxylated glycerol, polyethoxylated fatty acids and mono-, di- and triesters of glycerol that is polyethoxylated to different degrees (Müller K., 1996, *Tenside* 3, 37). B-H show the different molecular forms of polyethoxylated glycerol ricinoleate that possess both hydrophobic and hydrophilic parts. B-D represent the general structure of ricinoleic acid mono- and diesters (hydrophobic) in which the non-esterified OH of glycerol is bound to polyoxyethylene through ether bond (hydrophilic). E-H, general structures of polyethoxylated glycerol (hydrophilic) in which one, two, or all polyethylene residues are esterified by ricinoleic acid (hydrophobic). These formulas were constructed on the basis of published information (Müller, K., 1996, supra) and the technical information kindly provided by the manufacturer of Cremophor EL (BASF Corporation, Cosmetic Chemical Laboratories, Washington, N.J.).

The following injection concentrates were used: Taxo® (MeadJohnson Oncology Products, Bristol-Myers Squibb Co., Princeton, N.J.) containing 6 mg/ml paclitaxel and 527 mg/ml Cremophor EL® in 50% ethanol; Paraplatin® (Bristol-Myers Squibb Co., Princeton, N.J.) containing 50 mg/ml carboplatin and 50 mg/ml mannitol in $H_2O$); Sandimmune® (Sandoz Pharm. Co., East Hanover, N.J.) containing 50 mg/ml cyclosporine and 650 mg/ml Cremophor EL in 32.9% ethanol; Taxotere® (Rhone-Poulenc Rorer Pharm. Inc.) containing 40 mg/ml docetaxel in polysorbate 80 (Tween-80). The above agents were diluted either in phosphate buffered saline (PBS) or in 0.9% sodium chloride injection, USP (McGaw, Inc., Irvine, Calif.) to give 0.5 or 1 mg/ml stock with regard to the active ingredient. Cyclosporine was also used as a 10 mg/ml stock. Docetaxel stock solutions were prepared both in saline and in 50% ethanol. Cremophor EL®, the nonionic emulsifier vehicle of Taxol and cyclosporine, was purchased from Sigma Chem. Co. (St. Louis, Mo.) and was diluted in 50% ethanol to give a 527 mg/ml stock. As it is critical in the present study, FIG. 1 provides structural information on the molecules present in Cremophor EL (Muller, K., 1966, *Tenside* 3, 37).

Recombinant soluble complement receptor type 1 (sCR1) was kindly provided under a Material Transfer Agreement by T Cell Sciences, Inc. (Needham, Mass.).

Subjects and Collection of Serum Specimens

Non-anticoagulated blood was drawn from healthy volunteers and from cancer patients according to protocols approved, as additions to existing protocols, by the Walter Reed Army Medical Center Human Use Committee, and by the University of Southern California (USC)/Norris Cancer Center Institutional Review Board and General Clinical Research Center. The cancer patients (6 men and 4 women) were taking part in a phase I pharmacologic study evaluating treatment with Taxol for solid tumors utilizing an every 2 week dosage schedule, and gave written informed consent. In the present study no special effort was made to record hypersensitivity reactions to Taxol; the blood specimens were obtained before the first cycle of therapy, when patients had not received cytostatic treatment for at least 3 weeks. Blood was allowed to clot at room temperature and the serum was stored at −80° C. It was thawed and kept at 4° C. before incubation with the test agents.

Assay of in Vitro Complement Activation

To assess C activation in vitro we measured the drug-induced rise of two C split products, SC5b-9 and Bb, using ELISA kits from Quidel Corp. (San Diego, Calif.). SC5b-9 is the soluble, S-protein-bound form of the terminal complex, a sensitive measure of C5a formation through both the classical and the alternative pathways, while Bb is the proteolytically active fragment of factor B, a specific marker of C activation through the alternative pathway. The test agents were incubated with the serum in a shaking water bath (80 rpm cycle) for 30 to 60 min at 37° C. at an activator to serum volume ratio of 1:5 or 1:10. Typically, 5 µl of drug (stock) was added to 45 µl of serum placed in Eppendorf tubes. The reaction was stopped by adding 20 volume of the specimen diluent from the ELISA kits containing PBS, 0.05% Tween-20, protein stabilizers, and 0.01% Thimerosal.

Statistical Analysis

Data were subjected to Student's paired or unpaired, two-tailed t-test, as indicated for the respective experiments. Differences between groups were considered significant at $p<0.05$.

Closed Chest Instrumented Pig

Experiments were-performed in accordance with the guidelines of the Committee on Animal Care of the Uniformed Services University of the Health Sciences and with the Guide for the Care and the Use of Laboratory Animals (Department of Health and Human Services, Publication No. [NIH] 86-23). Female Yorkshire swine (32-48 kg) were sedated with i.m. ketamine and anesthetized with halothane by nose cone. The trachea was intubated and anesthesia was maintained with halothane (1%). A pulmonary artery catheter equipped with thermodilution-based continuous cardiac output detector (TDQ CCO, Abbott Laboratories, Chicago, Ill.) was advanced via the right internal jugular vein through the right atrium into the pulmonary artery to measure pulmonary artery pressure (PAP), central venous pressure (CVP) and cardiac output (CO). A 6FR Millar Mikro-Tip catheter (Millar Instruments, Houston Tex.) was inserted into the right femoral artery and advanced into the proximal aorta for blood sampling and to measure systemic arterial pressure (SAP). A second 6FR pig tail Millar Mikro-Tip catheter was inserted through the left femoral artery and placed into the left ventricle to monitor left ventricular end-diastolic pressure (LVEDP). Systemic vascular resistance (SVR) and pulmonary vascular resistance (PVR) were calculated from SAP, PAP, CO, CVP and LVEDP, using standard formulas (Fontana, J. L. et al., 1995, Anesth. Analg. 80, 219) Blood pressure values and leads II and V5 of the electrocardiogram (ECG) were obtained continually.

Preparation of Liposomes and Liposome-Encapsulated Hemoglobin

The preparation and characterisitics of large multilamellar liposomes consisting of dimyristoyl phosphatidylcholine, dimyristoyl phosphatidylglycerol, cholesterol (50:5:45 mole ratios) with 0.5% α-tocopherol and 40 mg/mL heat-sterilized, diaspirin-crosslinked human hemoglobin (in LEH), were described previously (Szebeni, J. et al., 1997, Transfusion, 37, 150) Liposomes were suspended in normal saline, or phosphate buffered saline (PBS) at 1-100 mg/mL lipid (1-100 mM phospholipid).

Experimental Protocol

Liposomes were injected in the jugular vein, most often in 1 mL boluses containing 5 mg lipid (3.4 mg phospholipid and 1.6 mg cholesterol). These injections were repeated several times at 20-60 min intervals. Before each injection and at 1 min intervals up to 10-15 min, and finally at 30 min, the hemodynamic parameters were recorded and arterial specimens (2-3 mL) were withdrawn into EDTA-containing vials for white blood cell (WBC) and platelet counting and for $CH_{50}$ and thromboxane $B_2$ ($TXB_2$) ELISA assays, as described previously (Szebeni, J. et al., 1994, Biochem. Biophys. Res. Comm. 205, 255). Blood was also collected for hemoglobin, arterial $O_2$, mixed venous $O_2$, pH, plasma $HCO_3$ and base excess measurements. These remained in the normal range throughout all studies presented.

Complement Activation in Pig Serum in Vitro and Testing of the Cardiovascular Effects of Activated Serum Two mL aliquots from freshly prepared pig serum was incubated with liposomes (10 mg/mL lipid) at 37° C. for 10 min in a shaking bath. After adding 4 volumes of PBS, the vesicles were pelleted by centrifugation at 4° C. for 10 min at 14,000 rpm, and the supernatant was immediately injected in the pigs as described above for liposomes.

Complement Antagonists

Murine anti-porcine C5a (GS1, Chemicon, Temecula, Calif.) was prepared from tissue culture or ascites, was purified by protein G affinity chromatography and dialyzed against PBS (purity: >95%). It was shown previously to inhibit C5a-induced porcine neutrophil aggregation with an $IC_{50}$ of 3 µg/mL, and to significantly inhibit polymorphonuclear leukocyte (PMN) chemotaxis at a dose of 17 µg/mL (Stahl, G. L. et al., 1997, FASEB J. 11, A331). Administration in pigs at 1.6 mg/kg maintains plasma GS1 levels above 40 µg/ml for at least 3 hours (Tofukuji, M. et al., 1998, J. Thor. Cardiovasc. Surg.).

Recombinant soluble complement receptor type 1 (sCR1, Weisman, H. F. et al., 1990, Science 249, 146) was obtained from T Cell Sciences, Inc. (Needham, Mass.). Its plasma clearance in pigs was reported to have α- and β-phase $t_{1/2}$ values of 8.3 and 363 min, respectively, with 31% of the drug clearing slowly (U.S. Pat. No. 5,456,909, Oct. 10, 1995). Previous in vitro studies showed sCR1 to significantly inhibit LEH-induced complement activation in human serum at doses >0.8 µg/mL, with 20 µg/mL providing complete suppression of SC5b-9 (S-protein-bound terminal complex) formation (Szebeni, J. et al., 1997, supra).

C5a Production and Immunoglobulin Binding by Liposomes in Vitro

Liposomes were incubated with pig serum (5 and 10 mM phospholipid) with or without 10 mM EGTA/2.5 mM $Mg^{++}$ for 10 min at 37° C. with shaking, and, after centrifugal separation of vesicles, C5a production was measured by a chemotaxis assay (Vakeva, A. P. et al., 1998, Circulation 97, 2259) To measure liposome-bound IgG and IgM, the vesicles were fixed in 1% paraformaldehyde (30 min, 4° C.), washed with PBS and stained with IgG and IgM class-specific anti-swine antibodies (Kirkegaard and Perry Laboratories (Gaithesburg, Md.). Fluorescence labeling was accomplished by incubation with 1:100 diluted fluorescein isothiocyanate (FITC)-conjugated F(ab)$_2$ (Jackson Immunoresearch, West Grove, Pa.) directed against the anti-swine antibodies. FACS analysis was performed in a FACSort flow cytometer and CellQuest software (Becton Dickenson, San Jose, Calif.). Live gating was set on the forward scatter (size) parameter with analysis for FITC fluorescence in arbitrary units.

Statistical Methods

Data are presented as means ±S.E.M., or for individual pigs. Differences were analyzed by Student's t-tests or by ANOVA followed by the Newman-Keul procedure. The fitting of non-linear equations was accomplished as described previously (Chaterjee, 1977, supra; Kang, Y. H. et al., 1992, supra) using the maximum likelihood algorithms of Gauss System 3.02 and Gaussx 3.0 (Aptech Sytems, Kent, Wash.), or Statistix 4.1 (NH Analytical Software, Roseville, Minn.). Confidence and standard errors of coefficients were obtained by computations of multiple regression coefficient ($R^2$), residual sum squares and Durban-Watson statistics for serial errors. The randomness of residuals was examined using the Wilk-Shapiro statistics (Statistix 4.1) or the heteroscedasticity routines of Gaussx 3.0.

EXAMPLE 1

Figure 2A:
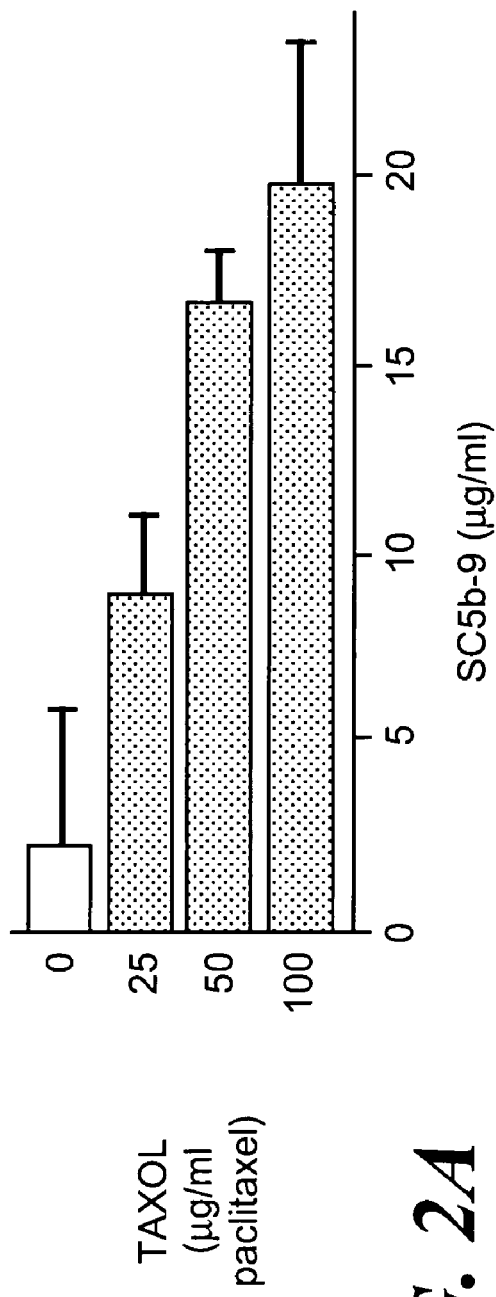
FIGS. 2A and B. The effects of Cremophor EL and Taxol on SC5b-9 formation in different sera obtained from healthy subjects and cancer patients. Paclitaxel (100 ug/mL) or a corresponding volume of phosphate-buffered saline (PBS) was incubated with serum samples from 10 healthy volunteers (five men and five women) (A) and 10 cancer patients (six men and four women) (B), and the level of SC5b-9 with 95% confidence interval for quadruplicate (healthy subjects) or triplicate (cancer patients) determinations following incubation with paclitaxel (filled bars) or PBS (empty bars). The difference between paclitaxel and PBS was statistically significant in all healthy sera at P<0.0001, except in subject 2, where P=0.0002. Among the cancer patients, the paclitaxel-induced increase of SC5b-9 was statistically significant in subjects 6-10 with P<0.0001. *, SC5b-9=67.4 (65.8-69) ug/ml.
Figure 2B:
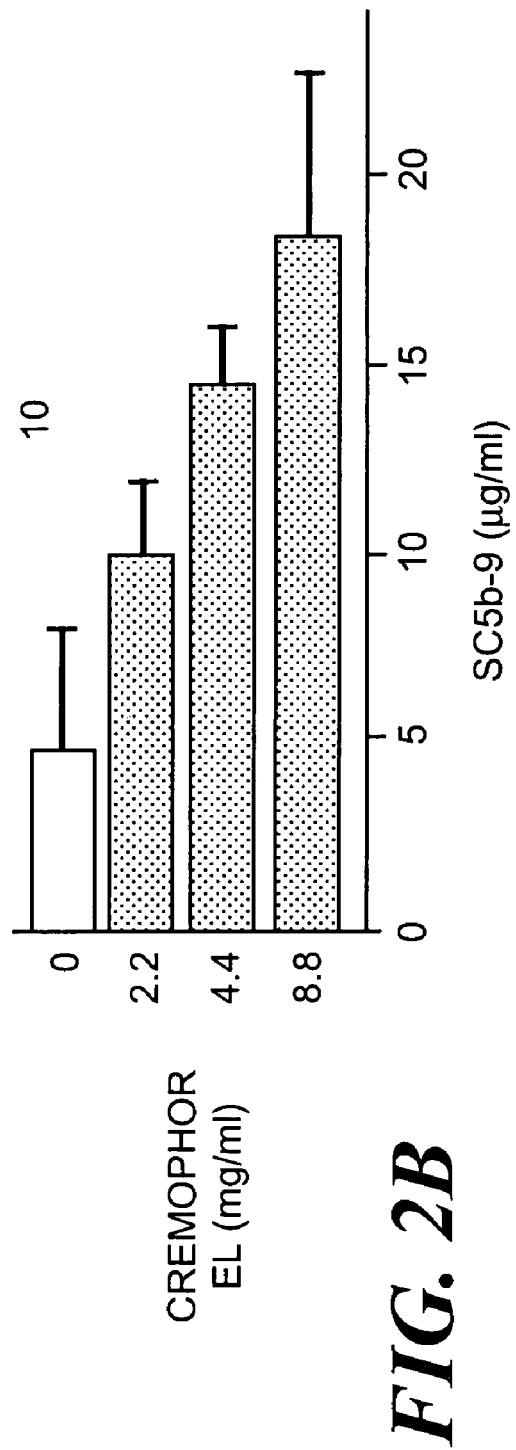

Complement Activation by Taxol and by Cremophor EL/ethanol in Normal Human Serum in Vitro FIG. 2A shows that incubation of a healthy serum specimen with increasing concentrations of Taxol (i.e. paclitaxel dissolved in Cremophor EL/50% ethanol) led to a significant concentration-dependent rise of SC5b-9 over baseline, providing evidence for C activation. In FIG. 2B, however, it is seen that this effect was not due to paclitaxel, but to its solvent, Cremophor EL/ethanol, as incubation of the same serum with matched amounts of an ethanolic solution of Cremophor EL caused essentially identical, concentration-dependent C activation.

EXAMPLE 2

Figure 3B:
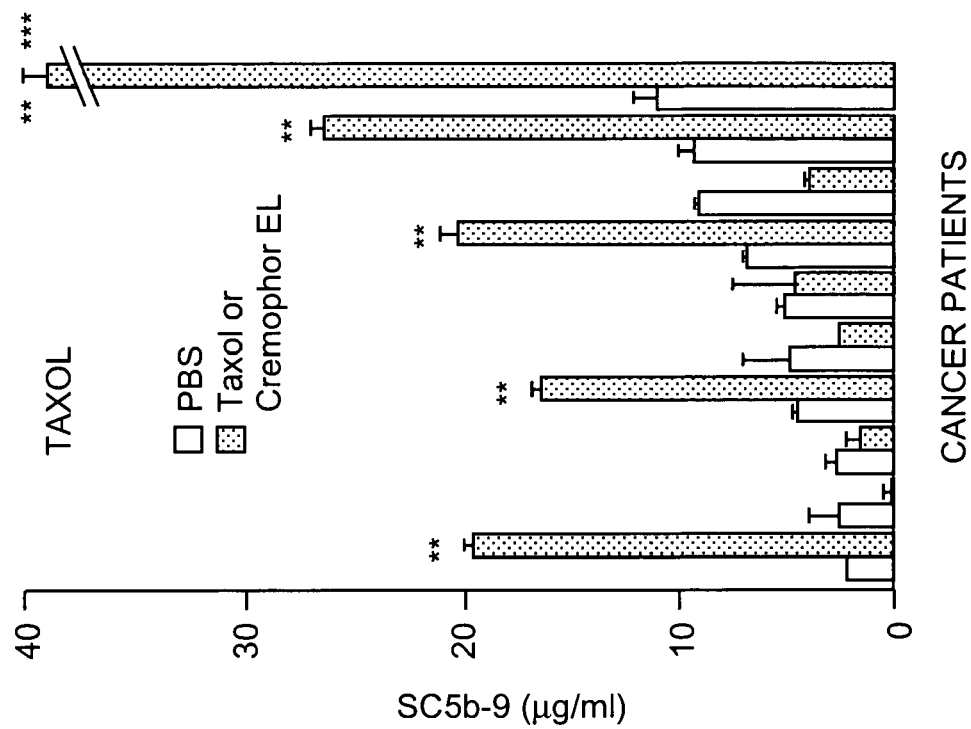
FIGS. 3A and B. Complement activation in human serum following incubation with paclitaxel or with its vehicle, Cremophor EL: dose effect relationship. The indicated concentrations of paclitaxel in Cremophor EL/ethanol (i.e., Taxol), or Cremophor EL in ethanol, were incubated with human serum, followed by measurement of SC5b-9 levels as described in "Materials and Methods" section. The concentrations were chosen on the basis that the Cremophor to paclitaxel weight ratio in Taxol is 88. Bars=mean concentrations of SC5b-9 with their 95% confidence intervals, obtained from triplicate wells.
Figure 3A:
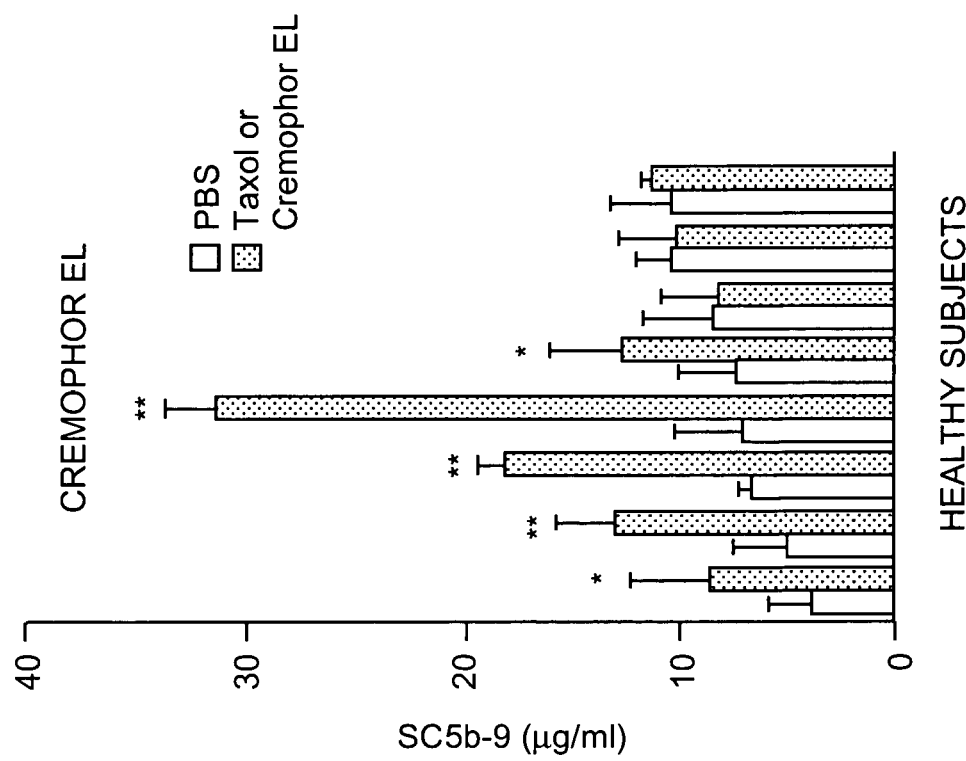
Figure 6C:
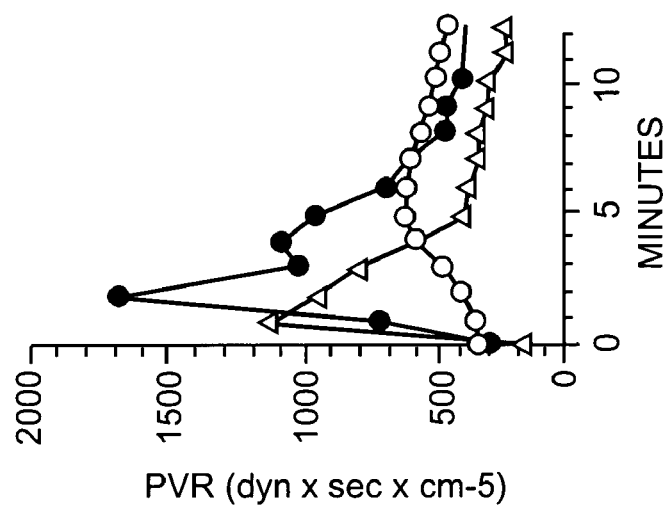
Figure 6B:
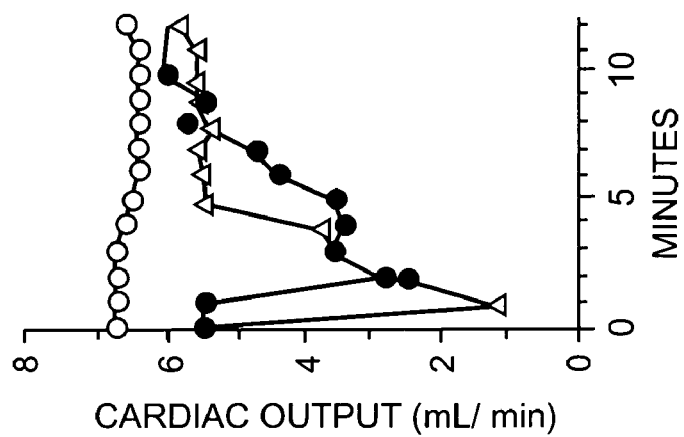
Figure 6A:
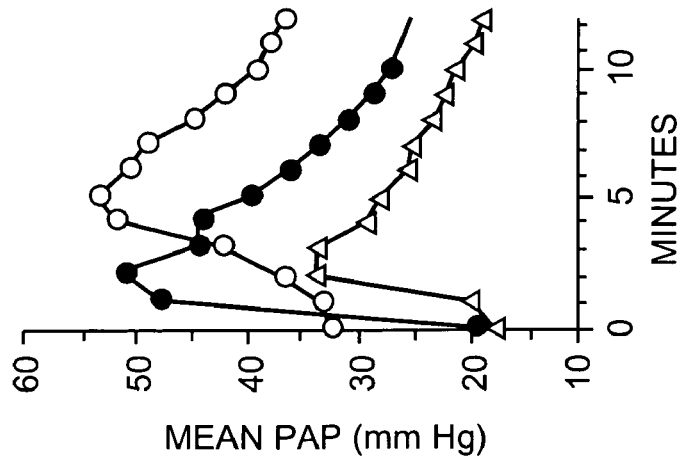
Figure 6F:
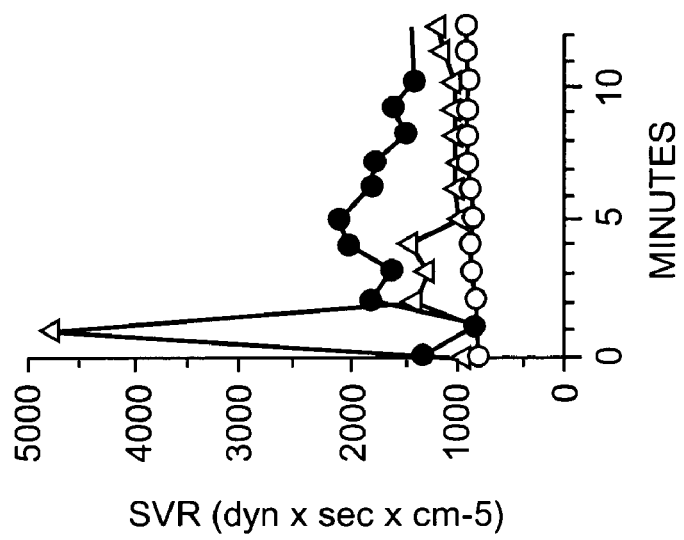
Figure 6E:
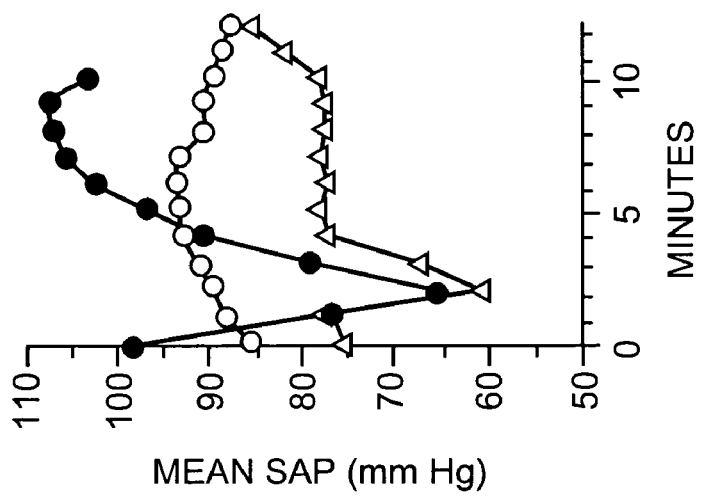
Figure 6D:
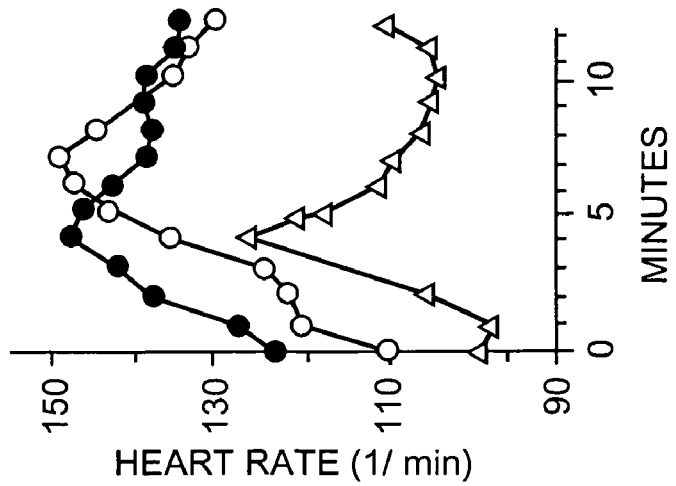

The Prevalence of Taxol and Cremophor EL/ethanol-induced Complement Activation in Vitro in Normal Subjects and in Cancer Patients To estimate the frequency of C reaction to Taxol under normal and pathological conditions, we have incubated Cremophor EL/ethanol with the sera of several normal individuals and Taxol with the sera of cancer patients. As shown in FIG. 3, the level of SC5b-9 was significantly increased in 3 of 8 normal and in 5 of 10 cancer patients, suggesting comparable prevalence of reactivity in the two groups. Importantly, these ratios were also comparable with the reported overall frequency of hypersensitivity reaction to Taxol in cancer patients (i.e., 41%) (Bristol-Myers Squibb Oncology Products Division, Princeton, N.J. Paxitaxel (Taxol) package insert. 1993).

FIG. 3 also reveals that the C response to Taxol or Cremophor EL considerably varied in the individual sera, with rises in SC5b-9 levels in the 2- to 10-fold range in reactive individuals, and significant declines below baseline in some non-reactive cancer subjects. The latter observation, however, was not explored further in the present study.

EXAMPLE 3

Definition of the Molecule(s) Responsible for Complement Activation

The conclusion from FIG. 2, i.e. that Cremophor EL together with 50% ethanol fully accounted for the C activation observed with Taxol, was further strengthened by the observation that cyclosporine, another drug that is formulated in Cremophor EL/ethanol, caused significant C activation in 2 of 3 tested human sera (Table 1).

Nevertheless these experiments did not provide information regarding the relative roles of Cremophor lipids and ethanol in the activation process. In an attempt to dissect the individual effects of these components, we have incubated human sera with 0.4-0.8% ethanol, concentrations that are present in the serum upon the addition of 50-100 μg/ml paclitaxel. As shown in Table 1, ethanol did not cause significant elevation of serum SC5b-9, leaving two alternatives; one is that C activation is solely due to the lipids, and second, that C activation is a result of the combined effects of ethanol and the lipids, with ethanol playing a potentiating role.

Although the latter possibility is not easy to prove directly (the highly viscous Cremophor EL is not miscible with serum), further control experiments provided support to the assumption that the presence of ethanol may be a precondition for the rise of massive C activation. As shown in Table 1, docetaxel (Taxotere, a structural analog of paclitaxel) caused C activation only when the drug (formulated in Tween-80) was added to human serum together with ethanol, but not when it was dissolved in $H_2O$.

Finally, Table 1 demonstrates that carboplatin, a water-soluble anticancer drug which is known to cause severe hypersensitivity reactions in cancer patients, did not cause C activation in either of the tested 2 Taxol-reactive sera.

EXAMPLE 4

The Pathway of Taxol-(Cremophor)-induced Complement Activation

To elucidate the mechanism of C activation described above, we have examined the effect of 10 mM EGTA/2.5 mM $Mg^{++}$ on Cremophor EL- and Taxol-induced rise of SC5b-9 and Bb in 3 subjects who displayed significant C response to these agents. The test is widely used to establish the pathway of C activation, as chelation of $Ca^{++}$ with the applied dose of EGTA inhibits classical pathway activation, while $Mg^{++}$ allows for the operation of alternative pathway, or even accelerates it. Detection of a rise in Bb levels, on the other hand, provides positive identification of alternative pathway activation.

TABLE 1

The effect of Taxol and different reference compounds on SC5b-9 formation in human serum

| | dose | Subjects | | | |
|---|---|---|---|---|---|
| | (μg/ml and %) | 1 | 2 | 3 | 4 |
| PBS | | 2.9 (2.7-3.0) | 3.6 (3.3-3.9) | 1.7 (1.6-1.7) | 7.5 (7.0-8.0) |

TABLE 1-continued

The effect of Taxol and different reference compounds on SC5b-9 formation in human serum

|  | dose (μg/ml and %) | Subjects | | | |
|---|---|---|---|---|---|
|  |  | 1 | 2 | 3 | 4 |
| Taxol (0.4% ethanol) | 50 |  |  | 3.6 (2.8-4.4)* |  |
| Taxol (0.8% ethanol) | 100 | 17.5 (17.0-18.0)** | 10.8 (10.6-11.0)** |  | 10.9 (10.2-11.6)** |
| cyclosporine | 50 |  |  | 3.1 2.5-3.7)* |  |
| cyclosporine | 1000 |  | 3.1 (3.0-3.2) |  | 22.0 (21.2-22.8)** |
| ethanol | 0.4% |  |  | 0.5 (0.4-0.6) |  |
| ethanol | 0.8% |  | 3.2 (2.9-3.5) |  | 6.6 (6.1-7.1) |
| docetaxel ($H_2O$) | 100 | 1.8 (1.7-1.9) |  | 0.2 (0-0.7) |  |
| docetaxel (0.8% ethanol) | 100 | 16.0 (15.1-16.9)** | 28.6 (27.4-29.8)** |  | 38.5 (37.1-39.9)** |
| carboplatin | 100 |  | 3.4 (2.9-3.9) |  | 5.5 (5.4-5.6) |

The indicated agents were incubated with the sera of 3 healthy donors (subject 1-3) and a cancer patients (subject 4) for 30 min at 37° C., and the level of SC5b-9 was determined by ELISA, as described in the Methods. Entries are μg/ml SC5b-9, mean with 95% confidence interval for triplicate determinations, except PBS in subject 3, where n = 2.
Ethanol percentages denote final serum concentrations;
*significant increase relative to PBS control at *, $P < 0.05$ or
**$P < 0.01$, as calculated by Student's two-sample t-test (two-tail).
The exact P values, where significant increases are indicated, are as follows: subject #1 (from top to bottom): $4.5 \times 10^{-7}$, $1.2 \times 10^{-5}$; subject #2: $2.5 \times 10^{-6}$, $2.4 \times 10^{-6}$; subject #3: 0.03, 0.03; subject #4: 0.002, $6.0 \times 10^{-65}$, $6.5 \times 10^{-5}$.

Table 2 shows that 1) the Cremophor and Taxol-induced increases in SC5b-9 formation were significantly suppressed, although not completely inhibited by EGTA/Mg$^{++}$, 2) that the rise of SC5b-9 was paralleled by a significant increase in serum Bb; and 3) that the formation of Bb was significantly enhanced in the presence of EGTA/Mg$^{++}$. Taken together, these data suggest that Cremophor EL-induced C activation involves both the classical and the alternative pathways. Since the acceleration of Bb production in the presence of EGTA/Mg$^{++}$ is a sign of classical pathway-independent operation of the alternative pathway, it is likely that Cremophor EL-induced alternative pathway activation can proceed both in conjunction with classical pathway activation (positive feedback loop), and also as an independent process.

TABLE 2

Pathway of complement activation induced in human serum by Cremophor EL or Taxol

|  | Subjects | | | | | |
|---|---|---|---|---|---|---|
|  | 1 | | 2 | | 3 | |
|  | SC5b-9 | Bb | SC5b-9 | Bb | SC5b-9 | Bb |
| PBS | 2.6 (1.1-4.0) | 4.7 (4.1-5.3) |  |  |  |  |
| Cremophor EL | 23.6 (23.0-24.2)** | 9.1 (7.7-10.5)* |  |  |  |  |
| CR. EL + E/Mg | 12.9 (12.5-13.3**§ | nd |  |  |  |  |
| PBS | 2.9 (2.7-3.0) | 2.9 (2.2-3.6) | 2.9 (2.7-3.0) | 3.1 (3.1-3.2) | 7.5 (7.1-8.0) | 6.2 (5.5-6.9) |
| Taxol | 17.5 (17.0-17.9)** | 4.6 (4.5-4.7)** | 13.1 (12.5-13.6)** | 4.1 (3.7-4.6)** | 10.9 (10.2-11.5)** | 8.5 (8.4-8.5)** |

TABLE 2-continued

Pathway of complement activation induced in human serum by Cremophor EL or Taxol

| | Subjects | | | | | |
|---|---|---|---|---|---|---|
| | 1 | | 2 | | 3 | |
| | SC5b-9 | Bb | SC5b-9 | Bb | SC5b-9 | Bb |
| Taxol + E/Mg | 5.0 (4.8-5.2)**§ | 6.1 (5.5-6.8)§§ | 7.7 (7.3-8.0)**§ | 6.7 (6.3-7.0)§§ | nd | 11.3 (10.7-11.8)§§ |

CR, Cremophor; E/M, EGTA/Mg$^{++}$.
The indicated agents were incubated with the sera of a healthy donor (subject 1) and two cancer patents (subjects 2 and 3), and the levels of SC5b-9 and Bb were determined by ELISA, as described in the Methods. Entries are µg/ml for both analytes, mean and 95% confidence interval for 3-4 wells. In the case of subject #1 incubations were done both with Cremophor EL and Taxol in two independent experiments.
The final concentrations of agents were: Cremophor EL, 8.8 mg/ml with 0.8% ethanol; Taxol, 100 µg/ml paclitaxel with 8.8 mg/ml Cremophor EL and 0.8% ethanol; EGTA, 10 mM; Mg$^{++}$, 2.5 mM;
nd, not done.
*, **, significant increases relative to PBS control at $P < 0.05$ and $P < 0.01$, respectively.
§significant decrease relative to Cremophor EL or Taxol;
§§significant increase relative to Taxol (and to PBS) (Student two-sample t-test, two-tail).
The exact P values, where significant differences in SC5b-9 levels are indicated are as follows (from top to bottom):
subject #1, upper panel: $9 \times 10^{-7}$, $2 \times 10^{-4}$, $1.4 \times 10^{-6}$; subject #1, lower panel: $4.5 \times 10^{-7}$, $6.7 \times 10^{-5}$, $1.1 \times 10^{-6}$; subject 2: $3.6 \times 10^{-6}$, $1.9 \times 10^{-5}$, $8 \times 10^{-5}$; subject 3, 0.013.
The P values where significant differences in Bb levels are indicated are as follows (from top to bottom): subject #1, 0.010, 0.003, 0.011; subject 2, 0.013, $4.2 \times 10^{-5}$, 0.001; subject 3, $4 \times 10^{-4}$, $1.3 \times 10^{-5}$, $2.2 \times 10^{-5}$.

EXAMPLE 5

Inhibition of Cremophor EL-induced Complement Activation in Vitro by Soluble Complement Receptor Type 1

As shown in FIG. 4, the Cremophor EL/ethanol-induced increase of SC5b-9 in human serum was significantly inhibited by sCR1 at doses >0.6 µg/ml, with 1.8 µg/ml providing complete suppression of the effect.

EXAMPLE 6

The Effect of Liposomes and LEH on Pulmonary and Systemic Circulation

FIG. 6 demonstrates typical hemodynamic responses to i.v. injections of 1 mL liposome boluses containing 5 mg lipid, defined as "standard" injection. These injections caused transient hemodynamic changes, including a 50-250% increase in PAP (panel A), zero to 80% decline in CO (panel B), a 2-6-fold increase in PVR (panel C), 5-10% increase in heart rate (panel D), 20-40% fall, or rise, or biphasic changes in SAP (panel E), and a zero to 400% rise of SVR (panel F). The reactions started within 1-2 minutes post-injection, reached their peaks within 5-6 minutes, and returned to baseline within 10-15 min.

Table 3 summarizes the hemodynamic changes in 18 pigs injected several times with the standard liposome or LEH boluses. The data, expressed as % change at the peak of response, show all liposome-induced changes to be significantly different from baseline (P<0.01, paired t-test), except for SAP. The hemodynamic effects of LEH and liposomes were not significantly different, although there was a tendency for higher increase and greater variability in PAP and PVR in the case of LEH.

In addition to the above changes, we also observed that the most intense reactions were associated with transient ST-segment depression on the ECG (data not shown), implying cardiac hypoxia. Furthermore, the most marked elevations of PAP and declines of CO were associated with an initial decline of SAP (FIG. 6E) with increased CVP and decreased LVEDP (data not shown), which point to increased PVR as the primary effect of liposomes. Regarding the increase in heart rate (FIG. 6D), the observation that it occurred independently of the changes in CO and/or SAP (FIGS. 6B and E) raises the possible involvement of mechanisms other than baroreflex response, for example coronary vasoconstriction and/or direct humoral effects (complement split products, catecholamines).

TABLE 3

Descriptive Statistics of Liposome- (A) and Liposome-Encapsulated Hemoglobin (B) Induced Hemodynamic Changes in Pigs

| | PAP (mm Hg) | CO (L/min) | PVR (dyn/sec/cm-5) | HR (1/min) | SAP (mm Hg) | SVR (dyn/sec/cm-5) |
|---|---|---|---|---|---|---|
| | % Change Relative to Baseline | | | | | |
| A) Liposomes | | | | | | |
| mean | 79 | −30 | 236 | 11 | −1 | 71 |
| S.E.M. | 9 | 7 | 54 | 2 | 4 | 27 |
| n of pigs (injections) | 18 (51) | 17 (48) | 17 (48) | 17 (48) | 18 (51) | 17 (48) |

TABLE 3-continued

Descriptive Statistics of Liposome- (A) and Liposome-Encapsulated Hemoglobin (B) Induced Hemodynamic Changes in Pigs

|  | PAP (mm Hg) | CO (L/min) | PVR (dyn/sec/cm-5) | HR (1/min) | SAP (mm Hg) | SVR (dyn/sec/cm-5) |
|---|---|---|---|---|---|---|
| minimum | 19 | −77 | 44 | −9 | −39 | −15 |
| maximum | 187 | 1 | 696 | 29 | 32 | 336 |
| P | $8 \times 10^{-8}$ | $8 \times 10^{-4}$ | $10^{-4}$ | $6 \times 10^{-4}$ | .81 | $2 \times 10^{-6}$ |
| B) LEH |  |  |  |  |  |  |
| mean | 103 | −38.4 | 466 | 13 | −10 | 84 |
| S.E.M. | 23 | 15.4 | 205 | 5 | 12 | 38 |
| n of pigs (injections) | 6 (8) | 6 (8) | 6 (8) | 6 (8) | 6 (8) | 6 (8) |
| minimum | 19 | −83.1 | 69 | 3 | −62 | 3 |
| maximum | 160 | −3.0 | 1375 | 35 | 9 | 226 |
| P | 0.3 | 0.6 | 0.1 | 0.6 | 0.4 | 0.8 |

Animals were repeatedly administered 1 ml liposomes (section A) or LEH (B) containing 5 mg lipid, and the changes in the indicated hemodynamic parameters were recorded before and at 1 to 5 min post-injection.
P values in section A compare the maximal changes with baseline, and were obtained with Student's paired t-test (two-tailed).
In section B P values compare LEH vs. liposomes using Student's two-sample t-test (two-tailed).

TABLE 4

Chemotaxis of Porcine Neutrophils to Liposome-Activated Porcine Sera

|  | Chemotaxis (x 0.1 mm) | |
|---|---|---|
| Experiments | I | II |
| serum | 3.44 ± 0.47 |  |
| serum + GS1 | 1.67 ± 0.20 (8)* |  |
| serum + EGTA/Mg++ |  | 0.71 ± 0.04 (8) |
| serum + liposomes | 4.90 ± 0.78 (8)* | 0.83 ± 0.03 (8)** |
| serum + liposomes + GS1 | 1.71 ± 0.22 (8)*, *** |  |
| serum + EGTA/Mg+++ liposomes |  | 0.70 ± 0.02 (8) |

Liposomes were incubated with two pigs' sera (experiment 1 and 2) and the chemotaxis assay was performed as described in the Methods. The liposome phospholipid concentrations in exp. 1 and 2 were 20 and 5 mM, respectively. GS1 was applied at 50 µg/mL, and EGTA/Mg++ at 10/2.5 mM.
*P < 0.05 compared to serum;
**P < 0.05 compared to serum + EGTA/Mg++ and serum + EGTA/Mg+++ liposomes;
***P < 0.05 compared to serum + liposomes.
Statistics were one way repeated measures ANOVA (Newman-Keuls test).

EXAMPLE 7

Dose-Response Relationship

FIG. 7A shows that the pulmonary hypertensive effect of liposomes displayed a sharp, near-linear dependence on lipid dose in the 0-20 mg range, with an estimated $ED_{50}$ of 4.5±1.4 (for statistical details see legend). This provided rationale for using 5 mg lipid boluses as standard test dose. Above about 20 mg lipid the dose-response curve flattened, indicating saturation of response. We also observed a dose-dependent change in the kinetics of PAP response, with swift, symmetric waves below about 20 mg lipid and protracted responses to 50 and 100 mg boluses (FIG. 7B).

EXAMPLE 8

Intra-Animal Reproducibility of Pulmonary Pressure Response

FIG. 8 shows that the 5 mg lipid boluses injected 9 times at 30-60 min intervals produced virtually identical rises in PAP (coefficient of variation: 11%) without tachyphylaxis. The lack of tachyphylaxis in pulmonary response to repeated low-dose liposome challenges was verified for most animals studied, by injecting the standard boluses 2-3 times, one at the beginning and one towards the end of the 6-8 hour experiments.

EXAMPLE 9

The Involvement of Serum in Mediating the Hemodynamic Effects of Liposomes

Intravenous administration of the pigs' own serum after in vitro incubation with liposomes (c.f. Methods) caused significant increases in PAP (65±16%, n=5 pigs), whereas native serum inocula, or those in which the complement system had been heat-inactivated before incubating with liposomes, caused no, or significantly less pulmonary hypertension (10±2% and 21±9%, respectively, n=4 pigs). These observations rule out physical blockage of pulmonary microcirculation by the large multilamellar liposomes as the sole cause of increased pulmonary vascular resistance, and point to an active role of heat-sensitive complement proteins in mediating the effect.

EXAMPLE 10

The Effect of Liposomes on Platelet, White Blood Cell and Serum Complement Levels FIG. 9 shows early (2-5 minutes), minor (5-18%) decreases in platelet counts in 4 of 8 tested animals (panel A), with paralleling, minor decline of WBC counts in 1 pig (panel B). Similar measurements following 2-3 subsequent liposome injections gave essentially identical results, with transient, <20% drops in these cells' counts. Measurement of hemolytic complement levels in pig sera before and at 5 and 30 minutes after the injection of standard liposome boluses indicated no significant complement consumption ($CH_{50}$/mL values were 147±28, n=6 pigs, 162±26, n=5 and 137±26, n=3, respectively).

EXAMPLE 11

Liposome-Induced Changes in Plasma Thromboxane $A_2$

FIG. 10A shows that the standard liposome boluses caused a massive (30-fold) increase in plasma levels of $TXB_2$ (the stable metabolite of $TXA_2$) on a time course that exactly coincided with the rise of PAP (Panel A). The second injection 30 min later (Panel B), or several injections over hours (Panel C), produced essentially identical, paralleling rises of PAP and $TXB_2$.

FIG. 11 shows a plot of PAP versus plasma $TXB_2$, all matched pre- and post-injection readings pooled from 7 pigs. The best fit (c.f. legend) is a sigmoid curve that shows no correlation between PAP and $TXB_2$ below about 1 ng/mL $TXB_2$, but strong, linear correlation above these values until the pulmonary response reaches saturation around 80 mm Hg. This model is consistent with $TXA_2$ playing a major role in the liposome-induced pulmonary hypertension.

EXAMPLE 12

The Effects of Complement Inhibitors and Indomethacin on Liposome-Induced Pulmonary Hypertension Direct evidence for a causal roles of both complement activation and $TXA_2$ release in liposome-induced pulmonary hypertension came from experiments using specific complement inhibitors; GS1 and sCR1, and the cyclooxygenase inhibitor, indomethacin. FIG. 12A shows that these agents inhibited the liposome-induced rises in PAP relative to the preinhibitor (baseline) response, most efficiently indomethacin. The suppression of pulmonary reactivity was not due to unrelated toxicity or tachyphylaxis, as the inhibitory effects of these agents could be overcome with larger liposome doses (illustrated for sCR1). FIG. 12B demonstrates the time points and extent of maximal inhibition that we observed in 4 pigs treated with each of the above inhibitors. It is seen that 5 mg/kg indomethacin completely suppressed the pulmonary reaction to 5 mg liposome boluses in all tested pigs, while 1.6 mg/kg GS1 exerted 25-60% inhibition, and 0.2 and 2 mg/kg sCR1 (in 2-2 pigs) caused 30-100% inhibition. These differences between pre- and post-inhibitor rises in PAP were significant ($P<0.01$) by Student's paired t-test.

EXAMPLE 13

The Pulmonary Effect of Zymosan

Injection of the (alternative pathway) complement activator, zymosan, in pigs in a fashion and dose level (5 mg) that simulated the administration of liposomes caused 53±13% increase in PAP (n=7 injections in 4 pigs) on a time course that was indistinguishable from that observed with the standard liposome injections.

EXAMPLE 14

In Vitro Studies on the Mechanism Liposome-Induced Complement Activation

Table 4 shows that: 1) Incubation of pig serum with liposomes in vitro increased the leukocyte chemotactic activity of serum; 2) this increase was inhibited in the presence of GS1; and 3) the chemotaxis-promoting effect of liposomes was inhibited by EGTA/$Mg^{++}$. The first two observations provide evidence that liposomes can trigger complement activation in pig blood with resultant production of C5a, while the inhibitory effect of EGTA/$Mg^{++}$ on this process shows that this activation was $Ca^{++}$-dependent, an attribute of classical pathway activation.

One possibility for complement activation by liposomes through the classical pathway is the binding of natural antilipid antibodies to the vesicles (Szebeni, J. et al., 1996, *Biochim. Biophys. Acta.* 1285, 127). FACS analysis of the amount of immunoglobulins on the surface of liposomes following exposure to pig serum indicated the binding of both IgG (FIG. 13/A) and IgM (FIG. 13/B) antibodies to the vesicles, implying that preconditions for classical pathway activation exist in pigs.

EXAMPLE 15

Correlation between complement activation and clinical symptoms of hypersensitivity to Doxil. 1-2 ml blood samples were taken into EDTA-containing collection tubes before, and at 10, 30, and 120 minutes after the start of Doxil infusion. Blood was then centrifuges at 4° C., and the plasma was stored at −70° C. until determination of SC5b-9 level by ELISA (Quidel, San Diego, Calif.). Patients were observed for at least 15-30 minutes inot the infusion and any subjective or objective sign of hypersensitivity reaction were recorded and scored.

Discussion

Cremophor-induced Hypersensitivity

As a first approach to explore the involvement of C in Taxol-induced hypersensitivity, we have incubated the sera of normal subjects and cancer patients with Taxol and appropriate controls, and measured the ensuing changes in C. The data indicated significant and quantitatively equal C activation by Taxol and Cremophor EL/50% ethanol, suggesting that the latter vehicle fully accounted for the C activating effect. The C reaction was significant in 3/8 normal and in 5/10 cancer patient sera, frequencies that are compatible with the prevalence of Taxol-induced minor hypersensitivity reactions in cancer patients (41-44%) (Bristol-Myers Squibb Oncology Products Division, Princeton, N.J. Paxitaxel (Taxol) package insert, 1993; Rowinsky, E. K., et al., 1993, supra; Weiss, R. B. et al., 1990, supra; Eisenhauer, E. A. et al., 1994, *J. Clin. Oncol.* 12, 2654). The applied concentration of Cremophor EL was also relevant clinically, as after dilution of the injection concentrate, Cremophor EL is infused into cancer patients at 26-106 mg/ml (Bristol-Myers Squibb Oncology Products Division, Princeton, N.J. Paxitaxel (Taxol) package insert, 1993), while the threshold concentration for C activation by Cremophor EL was 2.2 mg/ml in our in vitro experiments. Thus, during the time of Taxol infusion the patient's blood is continuously exposed to C-activating levels of Cremophor EL at the site of injection. The steady state plasma concentration of Cremophor EL (approximately 0.5 mg/ml or 1 μl/ml, Rischin, D. et al., 1996, *J. Natl. Cancer Inst.* 88, 1297), which is achieved after about 30 minutes into the infusion (Rischin, D. et al., 1996, supra), is probably irrelevant in these extrapolations, as C activation is a precipitous reaction that proceeds on a time scale of minutes.

Cremophor EL has been used as a vehicle in Taxol because of the poor water solubility of paclitaxel (Bristol-Myers Squibb Oncology Products Division, Princeton, N.J. Paxitaxel (Taxol) package insert, 1993; Rowinsky, E. K., et al., 1993, supra; Weiss, R. B. et al., 1990, supra). It has also been used as solvent for several other water-insoluble drugs, including althesin, cyclosporine, diazepam, didemnin E, echinomycin, propandid, teniposide and various steroid and multivitamin products. There are several reports of severe hypersensitivity reactions in man induced by the latter drugs (Sharma, A. et al., 1993, supra; Weiss, R. B. et al., 1990, supra; Lorenz, W. et al., 1977, *Agents Actions* 7, 63; Howrie, D. L. et al., 1985, *Drug Intell. Clin. Pharm.* 19, 425; Lassus, M. et al., 1985, *Proc. Annu. Meet. Am. Soc. Clin. Oncol.* 4, 268; Peereboom, D. M. et al., 1993, *J. Clin. Oncol.* 11, 885; Fossella, F. V. et al., 1995, *Semin. Oncol.* 22, 22), as well as by other agents dissolved in another polyethoxylated vegetable oil-based lipophilic solvent, Emulphor (Blum, R. H. et al., 1979, *Cancer Treat. Rep.* 63, 919; O'Dwyer, P. J. and Weiss, R., 1984, *Cancer Treat. Rep.* 68, 959; Athanassiou, A. E. et al., 1988, *J. Clin. Oncol.* 6, 1204). Concerning the cause of these acute reactions, fat embolization has been considered (Blum, R. H. et al. 1979, supra), but the possibility of C activation was never raised. The dog study, which demonstrated Cremophor EL-induced histamine release, showed oxyethylated oleic acid as the main culprit in the reaction (Lorenz, W. et al., 1977, supra).

As to the mechanism by which the Cremophor EL/ethanol pair induces C activation, ethanol was shown previously to cause increased C3 conversion in normal human serum, which was suggested to be due to inhibition of factor I (Laver, A. J. et al., 1995, *Biochem. Soc. Trans.* 23, 167S). Although ethanol alone did not account for the increase in SC5b-9 in our in vitro experiments, it is conceivable that the rise of SC5b-9 in reactive sera was due to the combined effects of Cremophor EL and ethanol, whereby C activation by the former agent was amplified in some way by ethanol, for example by inhibition of a C regulatory protein. This hypothesis is consistent with the observation that docetaxel led to significant C activation in human serum only when it was dissolved in ethanol. As with Taxol, the vehicle of docetaxel (polysorbate-80) has also been reported to cause hypersensitivity reaction in dogs (Essayan et al., 1996, supra), the clinical formulation also contains ethanol, and docetaxel has also been reported to cause hypersensitivity reactions in humans (Theis, J. G. et al., 1995, *J. Clin. Oncol.* 13, 2508). Furthermore, Carmustin, another antitumor agent which is dissolved in 10% ethanol, commonly causes some minor flushing during infusion.

In reviewing the observations which contradict to the implication of Cremophor EL in the hypersensitivity reaction to Taxol, the finding that Cremophor EL did not cause significant histamine release from human basophils (Essayan et al., 1996, supra) or from rat peritoneal mast cells (Decorti, G. et al., 1996, *Anticancer Res.* 16, 317) may be explained by the lack of C activation in vitro, as cell suspension media are normally decomplemented by heat inactivation. On the other hand, the evidence implicating paclitaxel as the cause of the reaction may not be conclusive: as discussed in the study of Essayan et al. (1996, supra), the release of histamine from basophils by paclitaxel was observed at paclitaxel levels 10 to 100-fold greater than the maximal concentrations given to patients, and it was not specific for basophils obtained from the patient who displayed hypersensitivity reaction to Taxol. The gap between the in vivo attainable and in vitro effective paclitaxel doses is further widened by the binding of 89-98% of paclitaxel to plasma proteins (Bristol-Myers Squibb Oncology Products Division, Princeton, N.J. Paxitaxel (Taxol) package insert, 1993). It should also be mentioned regarding the latter study (Essayan et al., 1996, supra) that the described successful desensitization of the patient to Taxol is not inconsistent with a C mechanism, as gradual decomplementation and/or repetitive induction of subclinical C activation could lead to tachyphylaxis (Marceau, F. et al., 1987, *Immunopharmacol.* 14, 67), i.e. temporary absence of response.

As to how Cremophor EL may trigger C activation by itself, previous studies by Hunter and Bennett (Hunter, R. L. and Bennett, B., 1984, *J. Immunol.* 133, 3167; Hunter, R. L. and Bennett, B. 1987, *Prog. Leuk. Biol.* 6, 181; Hunter, R. L. In: *New Generation Vaccines*, Levine M M (ed.) New York: Marcel Dekker, 1990) on the adjuvant properties of nonionic block copolymer surfactants, also known as Pluronic and Tetronic polyols, appear to be particularly relevant. As illustrated in FIG. 5A, two such molecules, designated L101 and L121, contain 6-7 units of ethylene oxide (polyoxyethylene or polyethoxy, POE blocks) that flank a long hydrophobic polyoxypropylene (POP) chain, forming a hydrophilic adhesive layer on the surface of oil droplets suspended in water (Hunter and Bennett, 1987, supra; Hunter, 1990, supra). These particles were found to bind proteins and to cause massive (57-66%) conversion of C3 in human serum through the alternative pathway (Hunter and Bennett, 1984, supra; Hunter and Bennett, 1987, supra). As shown in FIG. 1, Cremophor EL contains a great variety of polyethoxylated derivatives of glycerol ricinoleate mono-, di- and triesters, which possess both hydrophilic and hydrophobic parts (Muller, K., 1966, supra). FIG. 5B illustrates that these molecules distribute at the water-oil interface, exposing their unesterified hydroxyl and POE chains towards the water. Thus, molecules of Cremophor EL can form a hydrophilic adhesive layer on oil droplets in a fashion similar to that visualized for the block copolymers L102 and L121 (FIG. 5A) (Hunter, R. L. and Bennett, B., 1984,supra; Hunter, R. L. and Bennett, B. 1987, supra; Hunter, R. L., 1990, supra), suggesting that C activation could have the same mechanism: binding of C3 by POE residues at the water-oil interface (Hunter and Bennett, 1987, supra; Hunter, 1990, supra). It should be emphasized in this regard that hydroxyl groups on C-activating surfaces are the primary sites where C3b can covalently attach upon C activation. That molecules in the Cremophor EL/ethanol formulation can form self assemblies in water is consistent with the observation that they "tend to sink to the bottom of the (storage) vials if not vigorously mixed" (Theis, J. G. et al., 1995, supra).

In an attempt to explain the activation of the classical pathway by Cremophor EL, an extension of the above hypothesis predicts that in addition to C3, binding of naturally occurring anti-cholesterol antibodies to the hydroxyl-rich crust of Cremophor particles also takes place. The epitopes that these antibodies recognize contain the OH-group, these antibodies are abundant in most human plasma (Alving, C. R. and Swartz, G. M. 1991, *Crit. Rev. Immunol.* 10, 441), and were shown to lead to severe C-mediated hypersensitivity reaction in pigs subsequent to binding to cholesterol-containing liposomes (Wassef, N. M. et al. 1989, *J. Immunol.* 143, 2990).

Apart from the mechanism of C activation, the example of copolymers (and liposomes) may allow for another important intuitive conclusion regarding Cremophor EL. Hunter and Bennett have demonstrated that C activation by nonionic block copolymers significantly correlated with the efficacy of these polymers to act as immune adjuvants (Hunter and Bennett, 1987, supra). This observation therefore raises the possibility that Cremophor EL could act as an adjuvant in inducing immune response against paclitaxel or other drugs that it carries. If C activation is a major contributor to the hypersensitivity reactions to Taxol, then C inhibitors might provide specific prevention or therapy against the phenomenon. The presented in vitro results suggest that sCR1 could be particularly useful in this regard. This recombinant protein, a truncated soluble form of C receptor type I (CR1, CD35), inhibits C activation both by accelerating the decay of C3 and C5 convertases, and by acting as a cofactor for the proteolysis of C3b and C4b by factor I (Weisman, H. F. et al., 1990, *Science* 249, 146; Cheung, A. K. et al. 1994, *Kidney Int.* 46, 1680). Previous studies have shown sCR1 to be a potent inhibitor of C-mediated harmful effects in the 10-40 µg/ml (in vitro) concentration range (Cheung, A. K. et al. 1994, supra). Our study suggests that it can effectively inhibit Cremophor EL-induced C activation at even lower doses, a finding supporting the hypothesis that factor I inhibition could play a role in the effect of Cremophor EL/ethanol.

Liposome-induced Hypersensitivity

The advance of liposomal drugs into clinical trials brought to attention an unusual hypersensitivity reaction that includes hemodynamic changes with cardiopulmonary distress studies (Levine et al., 1991, supra; Ringden et al., 1994, supra; Laing et al., 1994, supra; Uziely et al., 1995, supra; de Marie, S., 1996, supra; Dezube, B. J., 1996, supra; Alberts and Garcia, 1997, supra). While the symptoms are manageable in most cases with corticosteroids and antihistamines, the reaction can be life-threatening in an occasional patient with history of allergy and cardiopulmonary disease (Levine et al., 1991, supra; Ringden et al., 1994, supra; Laing et al., 1994, supra; Dezube, B. J., 1996, supra; Alberts and Garcia, 1997, supra). The phenomenon has been called "pseudo-allergy" (Alberts and Garcia, 1997, supra), however, its mechanism has not been clarified, and, to our knowledge, has never been studied in an animal model.

The present study was initiated by previous observations in our laboratory on liposome-induced anaphylactoid reactions in miniature pigs (Wassef et al., 1989, supra). The liposomes in that previous study were the same as applied here, but were applied at a 500-fold higher dose and were injected slowly (3 to 5 min). The hemodynamic and $TXB_2$ changes were essentially similar, but were extended over 30-60 min postinjection and were associated with significant (36-38%) leukopenia and thrombocytopenia. Furthermore, unlike in the present study, repeat injections of liposomes caused sudden death in 3 of 4 animals (Wassef et al., 1989, supra). Thus, the reduction of liposome dose and change of administration protocol resulted in better control and reproducibility of the model.

Based on the hemodynamic and laboratory changes, as well as in vitro evidence of complement induced immune damage to liposomes, we proposed previously that the anaphylactoid reaction could be due to complement activation (Wassef et al., 1989, supra). The present work revisited this hypothesis and obtained numerous new support for the concept. These include the following observations: 1) the pulmonary response to liposomes was mediated by a heat-sensitive plasma factor; 2) zymosan imitated the hemodynamic effects of liposomes; 3) incubation of pig serum with liposomes in vitro led to the formation of C5a; 4) there was strong correlation between the liposome-induced rises in PAP and plasma $TXB_2$; and 5) specific complement inhibitors, GS1 and sCR1, caused significant inhibition of liposome-induced pulmonary hypertension. Among these findings the efficacy of complement inhibitors was of particular importance, as it provided direct evidence for a causal role of complement activation in the liposome-induced hemodynamic changes.

Regarding the mechanism of complement activation by liposomes, our in vitro studies suggested classical pathway activation due to the binding of naturally occurring IgG and IgM to the vesicles. Such liposome-reactive antibodies can bind to phospholipids and/or cholesterol in the bilayer membrane, and are abundant in the blood of animals and humans (Wassef et al., 1989, supra; Alving, C. R. and Swartz, G. M., 1991, *Crit. Rev. Immunol.* 10, 441). Nevertheless, the observation that the pulmonary effects of the alternative pathway activator zymosan were essentially identical to those of liposomes suggests that the pathway of activation could have no impact on the ensuing cardiopulmonary changes. The significance of highlighting the likely involvement of classical pathway activation in the process lies in the possibility to use complement inhibitors acting at the level of C1 (Liszewski, M. K., 1998, *Exp. Opin. Invest. Drug* 7, 323).

The extensive, often dramatic pulmonary changes in the face of undetectable complement consumption implies highly efficient coupling of complement signal to effector mechanisms. Our results suggest that this amplification is achieved through the action of $TXA_2$ released in the blood as a consequence of anaphylatoxin (and C5b-9) binding to macrophages, leukocytes, platelets, and possibly other cells (Marceau et al., 1987, supra; Hansch, G. M. et al., 1984, *J. Immunol.* 133, 2145; Stahl, G. et al., 1997, *Am. J. Physiol.* 272, C1821). Although complement activation can lead to marginalization, aggregation and microthrombus formation from PMN and platelets (Stahl, G. et al., 1997, *Am. J. Physiol.* 272, C1821; Martin, S. E. et al., 1988, *Circ. Res.* 63, 483), several observations in our study argue for eicosanoid-induced vasoconstriction, rather than microcirculatory blockage, as a major mechanism of liposome-induced pulmonary hypertension. These include 1) the lack of significant, or biologically meaningful thrombocytopenia and/or leukopenia; 2) the massive elevations of plasma $TXA_2$ proceeding in remarkable quantitative and temporal correlation with the rises of PAP; and 3) the complete suppression of pulmonary response by indomethacin, which inhibits eicosanoid production but not PMN-platelet aggregate formation. In fact, indomethacin did not inhibit the 36-38% leukopenic and thrombocytopenic effect of liposomes in our previous study, although it reduced the rise of PVR from 317% to 20% (Wassef et al., 1989, supra). Nevertheless it is possible that obstruction of microcirculation could contribute to the cardiopulmonary reaction to higher liposome doses, as suggested by the 20% persistent elevation of PVR despite treatment with indomethacin in our previous study (Wassef et al., 1989, supra), and the prolongation of hypertensive response to 50-100 mg lipid boluses in the present study. The relative contributions of these mechanisms to the cardiopulmonary reaction to higher lipid doses remain to be established, as well as the main cellular source of $TXA_2$.

In conclusion, the present study describes a porcine model that allows studying the cardiopulmonary manifestations of a clinically important, liposome-induced hypersensitivity reaction. We provide evidence that the reaction is due to complement activation and is mediated by $TXA_2$ and possibly other vasoactive eicosanoids. The high amplification of complement signal affords uniquely sensitive biocompatibility testing of liposomes and LEH, and potentially all other pharmaceutical products (e.g. colloidal dispersions, particulate biomaterials, radiocontrast agents and emulsifier-based drug vehicles, Szebeni, J. et al., 1998, *J. Natl. Cancer Inst.* 90, 300) that can cause similar reactions, tentatively called "complement activation-related pseudo-allergy" (CARPA).

What is claimed is:

1. A method for reducing symptoms of a complement-activation related immediate hypersensitivity reaction due to the presence of amphiphilic carrier comprising administering a composition comprising a hypersensitivity reducing amount of a complement activation inhibitor, a therapeutic amount of an active ingredient(s) and an amphiphilic carrier to a subject, wherein said amphiphilic carrier is polyethoxylated oil capable of causing an immediate hypersensitivity reaction in the subject, and wherein the complement activation inhibitor is selected from complement receptor type 1 derived protein(s), GS1, Factor H, Factor I, C1Inh, complstatin, anti-C5a, compound K-76COOH.

2. The method according to claim 1 wherein said composition further comprises a pharmaceutical solvent, emulsifier or detergent.

3. The method according to claim 2 wherein the pharmaceutical solvent is a hydrophilic or hydrophobic carrier vehicle.

4. The method according to claim 1 wherein the polyethoxylated oil is polyethoxylated castor oil.

5. The method of claim 1 wherein the administration includes: administering to said individual the complement activation inhibitor prior to the administration of said active ingredient.

6. The method according to claim 1 wherein said active ingredient is doxorubicin, daunorubicin or amphotericin B.

7. The method according to claim 1 wherein the active ingredient is hemoglobin or polynucleotides.

8. The method according to claim 1 wherein the complement activation inhibitor is GS1.

9. The method according to claim 1 wherein the active agent is paclitaxel, Doxil, althesin, cyclosporin, diazepham, didemnin E, echinomycin, propandid, steroids, teniposide, doxorubicin, daunorubicin, amphoterin B, hemoglobin, polynucleotide or multivitamin.

* * * * *